US012680135B2

(12) United States Patent
Slater et al.

(10) Patent No.: US 12,680,135 B2
(45) Date of Patent: Jul. 14, 2026

(54) DIAGNOSTIC ASSAY FOR TISSUE TRANSPLANTATION STATUS

(71) Applicant: Murdoch Childrens Research Institute, Parkville (AU)

(72) Inventors: Howard Robert Slater, Parkville (AU); Damien Luis Bruno, Airport West (AU); Devika Ganesamoorthy, Epping (AU)

(73) Assignee: Murdoch Childrens Research Institute, Parkville (AU)

( * ) Notice: Subject to any disclaimer, the term of this patent is extended or adjusted under 35 U.S.C. 154(b) by 0 days.

(21) Appl. No.: 18/167,807

(22) Filed: Feb. 10, 2023

(65) Prior Publication Data

US 2023/0193386 A1 Jun. 22, 2023

Related U.S. Application Data

(63) Continuation of application No. 16/871,951, filed on May 11, 2020, now abandoned, which is a continuation of application No. 15/675,466, filed on Aug. 11, 2017, now abandoned, which is a continuation of application No. 14/349,832, filed as application No. PCT/AU2012/001210 on Oct. 5, 2012, now abandoned.

(30) Foreign Application Priority Data

Oct. 7, 2011 (AU) ................................ 2011904235

(51) Int. Cl.
C12Q 1/68 (2018.01)
C12P 19/34 (2006.01)
C12Q 1/6881 (2018.01)

(52) U.S. Cl.
CPC ...... *C12Q 1/6881* (2013.01); *C12Q 2600/118* (2013.01); *C12Q 2600/156* (2013.01)

(58) Field of Classification Search
CPC ............ C12Q 1/6881; C12Q 2600/156; C12Q 2600/118; C12Q 2537/16
See application file for complete search history.

(56) References Cited

U.S. PATENT DOCUMENTS

2007/0111233 A1 5/2007 Bianchi et al.
2007/0259351 A1 * 11/2007 Chinitz .................. G16B 20/00
435/6.12
2011/0086347 A1 4/2011 Bruno et al.

FOREIGN PATENT DOCUMENTS

EP 1 325 963 A1 7/2003
WO WO 2011/057061 A1 5/2011
WO WO 2012/103031 A2 8/2012

OTHER PUBLICATIONS

F. Kaplan, et al. "Allele-specific Amplification of Genomic DNA for Detection of Deletion Mutations: Identification of a French-Canadian Tay-Sachs Mutation" J. Inher. Metab. Dis. 14 (1991) 707-714 (Year: 1991).*
Ruben D. Artero, et al. "Oligonucleotide probes detect splicing variants in situ in Drosophila embryos" Nucleic Acids Research, vol. 20, No. 21 5687-5690 (Year: 1992).*
Tony K.F. Yung, et al. "Single-Molecule Detection of Epidermal Growth Factor Receptor Mutations in Plasma by Microfluidics Digital PCR in Non-Small Cell Lung Cancer Patients" Clin Cancer Res 2009; 15(6) Mar. 15, 2009 (Year: 2009).*
Bruno, et al. 2014 "Use of copy No. deletion polymorphisms to assess DNA chimerism" *Clinical Chemistry* 60(8): 1105-1114.
Extended European Search Report in corresponding European Application No. EP12839093, dated Apr. 23, 2015.
Conrad, D.F. et al. 2010 "Origins and functional impact of copy number variation in the human genome" *Nature* 464: 704-712.
Hromadnikova, I. et al. 2009 The effect of DYS-14 copy number variations on extracellular fetal DNA quantification in maternal circulation *DNA and Cell Biology* 28:7, 351-358.
Li, et al. 2005 "Ready detection of donor-specific single-nucleotide polymorphisms in the urine of renal transplant recipients by matrix-assisted laser desorption/ionization time-of-flight mass spectrometry" *Clinical Chemistry* 51(10): 1903-1904.
Ling, et al. 2015 "A powerful new approach to measuring engraftment using copy number variations and droplet digital PCR, exemplified in a complex allogeneic bone marrow transplantation case" Roche Scientific Poster Display, *Pathology* 47: p. S87.
McCarroll, S.A. et al. 2008 "Integrated detection and population-genetic analysis of SNPs and copy number variation" *Nature Genetics* 40: 1166-1174.
Moreira, et al. 2009 "Cell-free DNA as a noninvasive acute rejection marker in renal transplantation" *Clinical Chemistry* 55(11): 1958-1966.
Snyder, et al. 2011 "Universal noninvasive detection of solid organ transplant rejection" *PNAS* 108(15): 6229-2634.
Ciurea, S.O. et al., 2009 "High Risk of Graft Failure in Patients with Anti-HLA Antibodies Undergoing Haploidentical Stem-Cell Transplantation" Transplantation 88(8): 1019-1024.
Qin. J. et al. 2008 "Studying copy number variations using a nanofluidic platform" Nucleic Acids Research 36(18): e116.

* cited by examiner

*Primary Examiner* — Stephen T Kapushoc
(74) *Attorney, Agent, or Firm* — Knobbe, Martens, Olson & Bear, LLP

(57) ABSTRACT

A method of detecting circulatory nucleic acids from a transplanted tissue in a transplant recipient, the method comprising: amplifying circulatory nucleic acids from a transplanted tissue in a blood sample from the transplant recipient, and detecting amplification of a copy number deletion (CND) polymorphism from the transplanted tissue, and related methods for determining the status of a donor tissue transplanted into a recipient.

6 Claims, 13 Drawing Sheets

DIAGNOSTIC ASSAY FOR TISSUE TRANSPLANTATION STATUS

FILING DATA

This application is a continuation of U.S. application Ser. No. 16/871,951, filed May 11, 2020, which is a continuation of U.S. application Ser. No. 15/675,466, filed Aug. 11, 2017, which is a continuation of U.S. application Ser. No. 14/349, 832, filed Apr. 4, 2014, which is the U.S. National Phase of International Application No. PCT/AU2012/001210, filed Oct. 5, 2012, designating the U.S. and published as WO 2013/049892 A1 on Apr. 11, 2013, which claims priority from Australian Provisional Patent Application No. 2011904235, filed on Oct. 7, 2011, entitled "Diagnostic assay for tissue transplantation status," the entire contents of which, are incorporated herein by reference.

FIELD

The present disclosure relates generally to tissue, including organ, transplantation. Taught herein is a genetic-based diagnostic assay to ascertain the status of a tissue transplantation procedure in a recipient based on a characterization of circulating or other cell free nucleic acid material. The instant disclosure enables kits, primers and protocols for ascertaining the status of a transplantation procedure.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Tissue, including organ, transplantation is an important medical procedure to replace diseased or traumatized tissue in a recipient patient with donor tissue from a genetically or histocompatibility matched donor. The success or otherwise of a transplantation procedure is currently determined mainly by an invasive histological examination of biopsied material. However, histological examination has a high degree of sampling error, is invasive, has low sensitivity, can potentially cause tissue damage, requires a high degree of technical expertise and is consequently expensive.

Worldwide, the number of patients requiring an organ transplant far exceeds the availability of suitable organs. An ability to identify early rejection of the transplanted organ would enable a physician to intervene with an appropriate immunosuppressive treatment and save the organ and potentially the patient's life. Reducing the level of organ failure due to rejection increases the availability of donor organs for other patients and significantly reduces the overall cost.

Kidney transplants account for over 50% of all organ transplants in Australia. This will likely increase over time with the number of patients receiving dialysis increasing at a rate of approximately 60% per year. In 2010, the cost of providing dialysis and kidney transplant services was approximately AU$1 billion (Howard et al. (2009) *Nephrology* 14:123-132; Cass et al. (2010) *Kidney Health Australia* 27).

The average cost of providing dialysis is AU$61,659 per person per year. This compares to AU$81,549 for a kidney transplant with subsequent costs of AU$11,770 per year. Hence, the ability to facilitate successful kidney transplants has significant economic benefits quite apart from the improved life expectancy and superior quality of life for successful kidney transplant recipients compared to those on dialysis.

The presence of circulating or cell-free DNA was first reported by Mandel et al. (1948) *C.R. Acad. Sci Paris* 142:241-243. Circulating DNA can arise following processes such as apoptosis and necrosis of tissue (Giacona et al. (1998) *Pancreas* 17:89-97). In patients with cancer, the circulating DNA can be identified as emanating from cancer cells on the basis of oncogenes, microsatellite altercations and other genetic biomarkers in the DNA (Diehl et al. (2005) *Proc. Natl. Acad. Sci USA* 102:16368-16373; Diehl et al. (2008) *Nat. Med.* 14:985-990). Hence, circulating DNA has been used in genotyping studies to detect disease conditions and as an indicator of the health of a person or a fetus.

International Patent Publication No. WO 2011/057061 proposed a genetic approach to monitor for the presence of DNA from donor tissue in a sample from the recipient. The method was based on determining a genetic profile of recipient and a donor DNA whereby the detection of free donor DNA provides an indication that donor cells were being destroyed. The approach proposed required, however, the genotyping of both the recipient and the donor in order to determine an appropriate genetic marker which was definitively donor nucleic acid. Furthermore, the genetic profile was principally focused on mutations or polymorphisms such as single nucleotide polymorphisms, variable number tandem repeats, minisatellites, di-, tri- and tetra-nucleotide polymorphisms and the like.

Lee et al. (2006) *Transfusion* 46:1870-1878 used bi-allelic insertion-deletion polymorphisms to characterize microchimerism. Subsequently, Abbott Laboratories produced a real-time PCR-based assay to detect 34 bi-allelic insertion-deletion polymorphisms.

Wu et al. (2009) *Nature Medicine* 15(2):215-219 used polymorphic deletion probes to identify and monitor cellular chimerism between recipient and donor tissue, mainly to ascertain the success or otherwise of stem cell engraftment. The authors proposed that deletion polymorphic detection would complement but not replace established techniques used for monitoring genetic chimerism. It was found that FISH-based polymorphic deletion probe analysis was not as sensitive as PCR-based short tandem-recipient analysis to detect levels of chimerization of less than 5%.

However, insertion-deletion polymorphisms are typically associated with small nucleotide deletions followed by a small number of nucleotide insertions (a few to tens of bp). In terms of their detection by PCR methodologies there is generally sharing of sequence identity between wild-type and indel alleles, which impacts (negatively) on the signal-to-noise ratio for quantification of DNA chimerism.

There is a clear need, therefore, to better manage tissue, including organ, transplantation procedures to ensure a high rate of transplant organ survival. This need is met by an ability to detect rejection at an early stage using a sensitive genetic-based approach.

SUMMARY

The present disclosure teaches a method for determining the status of donor tissue transplanted into a recipient, the method comprising screening a sample from the recipient for the presence or absence of circulating nucleic acids which have a copy number variant (CNV) polymorphism which indicates the nucleic acids are donor-derived nucleic acids wherein the presence of donor nucleic acids is indicative of cellular damage of transplanted tissue and the absence of donor nucleic acids or a level of donor nucleic acids relative to a control is indicative of no cellular damage or minimal or clinically acceptable cellular damage. In an embodiment, the CNV is a copy number deletion (CND) polymorphism which is one of a panel of CND polymorphisms wherein a given recipient is characterized by having a null genotype for at least one CND polymorphism in the panel and the donor transplant as having a non-null genotype for this CND polymorphism. In an embodiment, the genotype of the donor with respect to CND polymorphisms does not have to be directly determined. Furthermore, the presence or absence of the polymorphism need not be determined by nucleotide sequencing nor by bi-allelic microchimerism. Examples of CNV polymorphisms are listed in Table 2. In an embodiment, the CNVs are CNDs as listed in Table 3.

CNV is defined as a DNA sequence that varies in copy number within individuals in the population, the length of DNA sequence affected may vary from a few hundred base pairs to several million base pairs. Contrastingly, sequence-level deletions involve shorter sequences of DNA, typically in the range 1 bp to 100 bp. Insertion-deletion is described as a deletion of DNA sequence (usually a few base pairs) followed by an insertion of DNA sequence (usually a few base pairs) after the deleted nucleotides.

The use of CNV-deletion loci enables interrogation of large DNA sequences (by qPCR or other molecular methodology) that are absent in the recipient, thus completely avoiding the issue of distinguishing donor DNA from background recipient DNA and leading to improvements in the signal-to-noise ratio for measurement of target DNA levels.

Reference to "tissue" includes an organ, limb and appendage as well as microtissues and stem cells. Examples of organs include a kidney, heart, lung, pancreatic islet, liver, intestine and skin Examples of limbs include a leg, arm, hand and foot. Examples of an appendage include a toe, nose and ear. Examples of stem cells include adult and embryonic stem cells. The sample which is screened for free nucleic acids is selected from plasma, whole blood, serum, urine, pus, respiratory fluid, lymph fluid, feces, bile, saliva, sputum, semen, vaginal flow, cerebrospinal fluid, brain fluid, ascites, milk, secretions from the genitourinary tract and a lavage of a tissue or organ (e.g. a lung) In an embodiment, the sample is plasma, whole blood or serum. In an embodiment, the sample is urine. A "free" nucleic acid includes a circulating nucleic acid and refers to nucleic acid released following cell damage. Cell damage may result from processes such as apoptosis or necrosis, drug cytotoxicity or an immunologically-based rejection reaction.

Another aspect enabled herein is a transplantation protocol for transplanting tissue from a donor to a recipient, the protocol comprising transplanting the tissue and then monitoring a sample from the recipient for the presence of circulating nucleic acids which are from donor cells wherein if donor nucleic acids are detected, the recipient is subjected to immunosuppression therapy or, if the patient is on immunosuppression therapy, the therapy may be altered.

The subject disclosure further teaches an assay to monitor the balance between immunosuppression and tissue damage such as due to rejection or pharmaceutical cytotoxicity. Hence, the subject disclosure teaches a method of treating a subject who has undergone a transplantation procedure by monitoring for changes in the levels of donor nucleic acids. Such changes may be relative to a control. The control includes pre-transplantation levels of free recipient nucleic acids or a change in the ratio of total nucleic acids to donor nucleic acids.

Further provided is the use of a panel of CNVs such as CNDs which identifies a nucleic acid as being of donor origin or, by deduction, non-recipient origin in the manufacture of a diagnostic assay to detect the status of transplanted tissue in the recipient. In an embodiment, one of the recipient or donor has a null genotype with respect to at least one of the CND polymorphisms and the other of the recipient or donor does not.

Table 2 provides a list of common CNVs which are characteristic of in recipient DNA. The list in Table 2 should be read in conjunction with, and includes, other known CNVs such as those defined in Conrad et al. (2010) *Nature* 464:704-712; McCarroll et al. (2008) *Nat Genet* 40(10): 1166-1174. One group of 10 CNVs, in the form of CNDs is listed in Table 3. In an embodiment, at least one CND null genotype is present in any given recipient. The donor need not be genotyped as CND polymorphisms are selected such that there is approximately a 50% probability that if a recipient has a null-CND genotype, the donor will not. In transplant recipients experiencing variable clinical signs of rejection, the donor-specific plasma nucleic acid concentrations may vary which correlates with the immunologic mechanism of rejection (i.e. humoral versus cellular) as well as the medical category of rejection (i.e. acute versus chronic).

The following abbreviations used in the specification are defined in Table 1.

TABLE 1

| Abbreviations | |
| --- | --- |
| Abbreviation | Definition |
| AP-PCR | Arbitrarily primed PCR |
| cfDNA | Circulating, free DNA |
| CND | Copy number deletion |
| CNV | Copy number variant |
| CP-PCR | Consensus sequence primed PCR |
| DOP-PCR | Degenerate oligonucleotide-primer PCR |
| MF-PCR | Multiplex fluorescent PCR |
| PCR | Polymerase chain reaction |
| PCR/RFLP | Restriction fragment length PCR |
| q-PCR | Quantitative PCR |
| qf-PCR | Quantitative fluorescent PCR |
| RT-PCR | Real time PCR |
| NABSA | Nucleic acid based sequence amplification |
| Null genotype | Zero copies of a genetic marker (nullisomic) |
| SRY | Sex-determining region Y |

BRIEF DESCRIPTION OF THE FIGURES

Reference is made to a "CND_0X" were X is a numeral from 1 to 10. These are CNVs which are defined in Table 3 and are selected from Table 2.

DETAILED DESCRIPTION

Figure 1A:
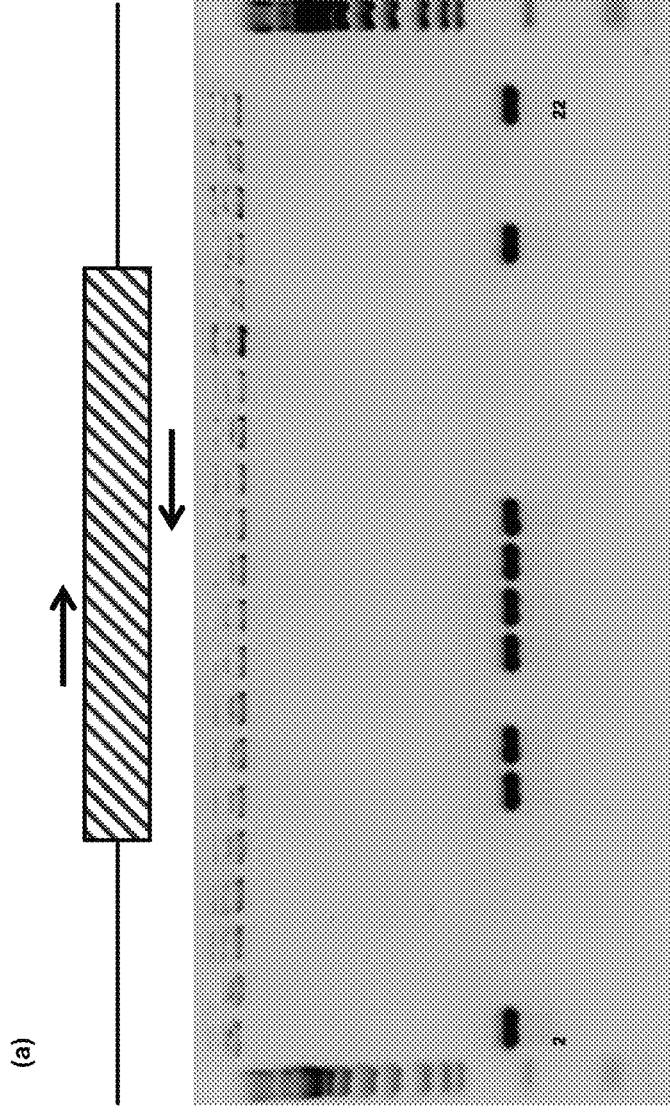
FIG. 1a is a diagrammatic and photographic representation of CND_01 internal PCR: Shaded region indicates the deleted segment. Lanes 2-22 are 21 control samples (12/21-null copy, 9/21-1 or 2 copy), lanes 1 and 24—Marker VIII and lane 23-blank.

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include singular and plural aspects unless the context clearly dictates otherwise. Thus, for example, reference to "copy number variant" includes a single copy number variant, as well as two or more different copy number variants; reference to "an organ" includes a single organ, as well as two or more organs; reference to "the disclosure" includes single or multiple aspects taught by the disclosure; and so forth. The aspects taught and enabled herein are encompassed by the term "invention". All such aspects are enabled within the width of the claims.

The present disclosure teaches a non-invasive assay to assess the outcome of a tissue transplantation procedure. The assay relies on the identification of non-recipient nucleic acids (i.e. donor nucleic acids) in a biological sample from the recipient of transplanted tissue from the donor. By "identification" includes characterization and quantitation. The assay characterizes a copy number variant (CNV) polymorphism, such as a copy number deletion (CND), which identifies donor nucleic acid in a mixture of recipient nucleic acid in the sample. The CNV such as CND does not require sequence analysis or bi-allelic microchimerism analysis. Damage to a transplanted tissue elicits release of donor nucleic acids from the transplanted cells into the circulatory system and other fluids of the recipient. The status of the transplanted tissue can be monitored and early signs of cellular damage identified leading to appropriate clinical intervention to save the tissue. Cellular damage can result from inter alia immunological-based rejection, apoptosis, necrosis, pharmacological cytotoxicity, trauma, blood flow ischemia and infection. The clinical intervention may involve the administration of immunosuppressive drugs, if the patient is on immunosuppression therapy, a change in dose of the drug or the type of drug. Other interventions include anti-pathogen therapy, drugs to improve blood flow or protocols to reduce swelling or trauma to the tissue. The assay may be universally applied to all transplantation procedures without need of directly determining a donor's CNV polymorphism genotype. The detection of a CNV polymorphism enables a highly sensitive approach of identifying non-recipient human DNA. In an embodiment, the recipient has a null genotype with respect to the CNV polymorphism and the donor does not. Alternatively, the donor has a null genotype with respect to the CNV polymorphism and the recipient does not.

A CNV is a structural genomic variant, measuring 1 kb in length or larger (e.g. $1 \text{ kb-}10^8$ kb), that results in confined copy number changes in a specific chromosomal region. If its population allele frequency is less than 1%, it is referred to as variants (CNVs) include insertions and deletions as well as more complex changes that involve gains and losses at the same locus. CNV was originally defined as insertions and deletions greater than 1 kb in size (Feuk et al. (2006) *Nature Rev* 7:85-97). Over time, with the wealth of data emerging from the sequencing of human genomes (The 1000 Genomes Project Consortium (2010) *Nature* 467: 1061-1073), the operational spectrum of copy number variant (CNVs) has widened to include much smaller events (for example, those >50 bp in length). These are distinguished from small sequence deletion polymorphisms (also called single base changes) by their genomic size (Weber et al. (2002) *Am J Human Genet* 71:854-862).

The CNV polymorphisms are selected on the basis that due to their high incidence in the population, a recipient will be characterized as having nucleic acids with at least one CNV genotype and a 50% likelihood that if a recipient or donor has a given CNV genotype, then the other of the recipient or donor will not. In an embodiment, the recipient nucleic acid is characterized as being nullisomic for at least one of the CNV sites and the donor is not.

Accordingly, the present disclosure teaches a method for determining the status of a donor tissue transplanted into a recipient, the method comprising screening a sample from the recipient for the presence or absence of circulating nucleic acids which have a copy number variant (CNV) polymorphism which indicates it is donor nucleic acids wherein the presence of donor nucleic acids is indicative of cellular damage of the transplanted tissue and the absence of donor nucleic acids or a level of donor nucleic acids relative to a control is indicative of no cellular damage or cellular damage to an acceptable level. An "acceptable level" means minimal adverse clinical side effects.

The detection of donor nucleic acids means the detection of non-recipient-derived nucleic acid material which in turn is indicative of transplant rejection or other damage to the transplant including apoptosis, necrosis, ischemia, trauma or infection. The damage may also be due to a drug administered to the patient such as an immunosuppression drug. The absence of donor nucleic acids means that non-recipient nucleic acid material is not being released which is indicative of a successful or healthy transplantation. The CNV polymorphism genotype of the donor does not need to be determined for the assay to be effective. A panel of CNV polymorphisms is screened on the basis that any given recipient will have or not have at least one of these polymorphisms and the donor will have or not have one polymorphism different from the recipient. In an embodiment, the recipient is nullisomic for at least one of the CNV sites in the panel and the donor is not. In another embodiment, the donor is nullisomic for at least one of the CNV sites in the panel and the recipient is not. Furthermore, in transplant recipients experiencing variable clinical signs of rejection, the donor-specific plasma nucleic acid concentrations may vary which correlates with the immunologic mechanism of rejection (i.e. humoral versus cellular) as well as the medical category of rejection (i.e. acute versus chronic).

Consequently, the present specification is instructional for a method for determining the status of a donor tissue transplanted into a recipient, the method comprising screening circulating nucleic acids in sample from the recipient for the presence of a CNV polymorphism selected from a panel of polymorphisms wherein the donor nucleic acids comprise the presence or absence of at least one polymorphism not shared by the recipient wherein the presence of donor nucleic acids is indicative of cellular damage of the transplanted tissue and the absence of non-recipient nucleic acids or a level of non-recipient nucleic acids relative to a control is indicative of no cellular damage or cellular damage to an acceptable level for such as but not limited to the continued health of a patient.

In a related embodiment, the present specification enables a method for determining the status of a donor tissue transplanted into a recipient, the method comprising selecting a panel of from 1 to 200 oligonucleotide primer pairs which target from 1 to 200 known CNV polymorphisms, screening a sample from the recipient for the presence of circulating nucleic acids with the presence of nucleic acids with the from 1 to 200 oligonucleotide primer pairs wherein the donor nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of cellular damage of the transplanted tissue and the absence of non-recipient nucleic acids or a level of non-recipient nucleic acids relative to a control is indicative of no cellular damage or cellular damage to an acceptable level. In an embodiment, the panel comprises 1 to 100 oligonucleotide pairs targeting from 1 to 100 CNV polymorphisms. In an embodiment, there are from 1 to 10 oligonucleotide pairs targeting 1 to 10 CNV polymorphisms. By "1 to 200" means 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200.

Reference to "tissue" with regards to transplantation includes an organ, limb, appendage and skin as well as microtissue and stem cells. Examples of organs include kidney, heart, lung, pancreatic islet, liver, intestine and skin. A limb includes a leg, arm, hand and foot. An appendage includes a toe, nose and ear.

In an embodiment, the tissue is an organ selected from the list consisting of a kidney, heart, lung, pancreatic islet, liver, intestine and skin.

Hence, the present disclosure teaches a method for determining the status of donor organ transplanted into a recipient, the method comprising screening a sample from the recipient for the presence or absence of circulating nucleic acids which have a CNV polymorphism which indicates it is not the recipient's nucleic acids wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

The present specification is further instructional for a method for determining the status of a donor organ transplanted into a recipient, the method comprising screening circulating nucleic acids in a sample from the recipient for the presence of CNV polymorphism selected from a panel of polymorphisms wherein the recipient's nucleic acids comprise the presence or absence of at least one polymorphism not shared by the donor wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

In an embodiment, the present specification enables a method for determining the status of a donor organ transplanted into a recipient, the method comprising selecting a panel of from 1 to 200 oligonucleotide primer pairs which target from 1 to 200 known CNV polymorphisms, screening a sample from the recipient for the presence of circulating nucleic acids with the presence of nucleic acids with the from 1 to 200 oligonucleotide primer pairs wherein the recipient nucleic acids are characterized as having or not having at least one of the known CNV polymorphisms from the panel and the donor nucleic acids are distinguished from the donor on the basis of having or not having the polymorphism shared by the recipient, wherein the presence of donor nucleic acids is indicative of cellular damage of the transplanted tissue and the absence of non-recipient nucleic acids or a level of non-recipient nucleic acids relative to a control is indicative of no cellular damage or cellular damage to an acceptable level.

In an embodiment, the present specification enables a method for determining the status of a donor organ transplanted into a recipient, the method comprising selecting a panel of from 1 to 100 oligonucleotide primer pairs which target from 1 to 100 known CNV polymorphisms, screening a sample from the recipient for the presence of circulating nucleic acids with the presence of nucleic acids with the from 1 to 100 oligonucleotide primer pairs wherein the recipient nucleic acids are characterized as having or not having at least one of the known CNV polymorphisms from the panel and the donor nucleic acids are distinguished from the donor on the basis of having or not having the polymorphism shared by the recipient, wherein the presence of donor nucleic acids is indicative of cellular damage of the transplanted tissue and the absence of non-recipient nucleic acids or a level of non-recipient nucleic acids relative to a control is indicative of no cellular damage or cellular damage to an acceptable level.

In an embodiment, the present specification enables a method for determining the status of a donor organ transplanted into a recipient, the method comprising selecting a panel of from 1 to 10 oligonucleotide primer pairs which target from 1 to 10 known CNV polymorphisms, screening a sample from the recipient for the presence of circulating nucleic acids with the presence of nucleic acids with the from 1 to 10 oligonucleotide primer pairs wherein the recipient nucleic acids are characterized as having or not having at least one of the known CNV polymorphisms from the panel and the donor nucleic acids are distinguished from the donor on the basis of having or not having the polymorphism shared by the recipient, wherein the presence of donor nucleic acids is indicative of cellular damage of the transplanted tissue and the absence of non-recipient nucleic acids or a level of non-recipient nucleic acids relative to a control is indicative of no cellular damage or cellular damage to an acceptable level.

In an embodiment, the tissue is an organ selected from the list consisting of a kidney, heart, lung, pancreatic islet, liver, intestine and skin.

In an embodiment, the organ is a kidney.

Accordingly, the present disclosure teaches a method for determining the status of a donor kidney transplanted into a recipient, the method comprising screening a sample from the recipient for the presence or absence of circulating nucleic acids which have a CNV polymorphism which indicates it is not the recipient's nucleic acids wherein the presence of non-recipient nucleic acids is indicative of cellular damage of the transplanted tissue and the absence of non-recipient nucleic acids or a level of non-recipient nucleic acids relative to a control is indicative of no cellular damage or cellular damage to an acceptable level for the continued health of a patient. By "non-recipient" means "donor".

The present specification is also instructional for a method for determining the status of a donor kidney transplanted into a recipient, the method comprising screening circulating nucleic acids in sample from the recipient for the presence of CNV polymorphism selected from a panel of polymorphisms wherein the recipient's nucleic acids comprise the presence or absence of at least one polymorphism not shared by the donor wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

In an embodiment, the present specification enables a method for determining the status of a donor kidney transplanted into a recipient, the method comprising selecting a panel of from 1 to 200 oligonucleotide primer pairs which target from 1 to 200 known CNV polymorphisms, screening a sample from the recipient for the presence of circulating nucleic acids with the presence of nucleic acids with the from 1 to 200 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of cellular damage of the transplanted tissue and the absence of non-recipient nucleic acids or a level of non-recipient nucleic acids relative to a control is indicative of no cellular damage or cellular damage to an acceptable level for the continued health of a patient.

In an embodiment, the present specification enables a method for determining the status of a donor kidney transplanted into a recipient, the method comprising selecting a panel of from 1 to 100 oligonucleotide primer pairs which target from 1 to 100 known CNV polymorphisms, screening a sample from the recipient for the presence of circulating nucleic acids with the presence of nucleic acids with the from 1 to 100 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of cellular damage of the transplanted tissue and the absence of non-recipient nucleic acids or a level of non-recipient nucleic acids relative to a control is indicative of no cellular damage or cellular damage to an acceptable level for the continued health of a patient.

In an embodiment, the present specification enables a method for determining the status of a donor kidney transplanted into a recipient, the method comprising selecting a panel of from 1 to 10 oligonucleotide primer pairs which target from 1 to 10 known CNV polymorphisms, screening a sample from the recipient for the presence of circulating nucleic acids with the presence of nucleic acids with the from 1 to 10 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of cellular damage of the transplanted tissue and the absence of non-recipient nucleic acids or a level of non-recipient nucleic acids relative to a control is indicative of no cellular damage or cellular damage to an acceptable level for the continued health of a patient.

The "status" of the transplanted tissue means the presence or absence of any cellular damage to transplanted tissue. The presence of tissue damage is indicated by release of nucleic acids from cells of the donor tissue transplanted into the recipient. The status is the outcome of the assay. The released nucleic acids are referred to herein as "free" or "circulating" nucleic acids (e.g. circulating, free DNA [cfDNA]). The sample includes plasma, whole blood, serum, urine, pus, respiratory fluid, lymph fluid, feces, bile, saliva, sputum, semen, vaginal flow, cerebrospinal fluid, brain fluid, ascites, milk, secretions from the genitourinary tract and a lavage of a tissue or organ (e.g. a lung). In an embodiment, the sample is plasma, whole blood or serum. In an embodiment, the sample is urine. Hence, aspects contemplated herein include assaying biological fluid for circulating, free nucleic acids, such as cfDNA.

A "free" nucleic acid includes a circulating nucleic acid (e.g. cfDNA) and refers to nucleic acid released following cell damage. Cell damage may result from processes such as inter alia apoptosis or necrosis, drug cytotoxicity or an immunologically-based rejection reaction.

The assay is based on detection at the level of presence or absence of non-recipient (i.e. donor-derived) nucleic acids. The levels of donor-derived nucleic acids may also be monitored over time such as following transplantation or following administration of immunosuppression drugs or other therapies. Detection of donor-derived nucleic acids may also be used to assess the likelihood that the transplanted tissue will survive or will require removal and/or to assess the toxicity of a drug being given to a patient. Tissue damage includes immunological rejection, apoptosis, necrosis, trauma, ischemic injury, infection by a pathogen, perioperative ischemia, reperfusion injury, hypertension, injuries due to reactive oxygen species and pharmaceutical toxicity.

Terms such as "diagnosis", "prognosis", "determination", "monitor", "assay" and the like may be used to describe the methodology of detecting donor nucleic acids or nucleic acids which are not of recipient origin. The diagnostic assay may also be used in a protocol to monitor the health of a patient with respect to the status of the transplanted tissue and/or the level of toxicity of any drugs being administered to the patient.

Hence, the method enabled herein provides a means for assessing the transplant status or outcome. The status or outcome may range from transplant rejection to transplant tolerance or to any form of cellular damage. Tissue damage is evidenced by detection of non-recipient (i.e. donor tissue-derived) nucleic acids. These are released into various fluids in the recipient following apoptosis of cells of the donor tissue. Transplantation tolerance or non-damage tissue is evidenced by an absence of donor-derived nucleic acids or a level of donor-derived nucleic acids which relative to a control is indicative of minimal cell damage or a level of cell damage which is clinically acceptable for the continued health of the patient. Evidence for transplantation tolerance provides an indication that the transplant will likely survive or is at lest healthy at any given time period.

As used herein, the diagnosis or prognosis of transplant status includes predicting, assessing, determining and diagnosing transplant status or outcome and in some cases the likelihood that a patient will survive a transplantation procedure or post-transplantation medical protocol.

The CNV polymorphism may be a deletion, insertion or an expansion. In an embodiment, it is a CNV deletion, referred to herein as a copy number deletion CND or CND polymorphism.

A panel of CNV deletions is selected which is expected to have approximate null frequencies of 40-50% in the general population. This is done by in silico analysis of public data (Conrad et al. (2010) supra; McCarroll et al. (2008) supra). These CNV regions are polymorphic and have no intrinsic clinical significance. CNV selection and frequency calculations are performed as follows: The HapMap data set includes trio-data for each CNV. For frequency calculations, only singleton and parental samples are included. CNVs with only 0, 1 and 2 copy genotypes are selected for analysis (i.e. CNVs of more than 2 copy and Chromosomes X and Y CNVs are excluded). For each selected CNV, frequencies of 0, 1 and 2 copy genotypes are calculated. CNVs in the form of CNDs overlapping with segmental duplications were excluded. CNVs with 0.4-0.5 null copy frequency and less than 3 kb in size were selected from Table 2. An example is the CNDs listed in Table 3.

Table 2 provides a list of common CNV sites which are commonly present in recipient nucleic acid. The list in Table 2 should be read in conjunction with, and includes, other known CNVs such as those defined in Conrad et al. (2010) supra; McCarroll et al. (2008) supra. Included herein is an aspect whereby the recipient is nullisomic for at least one of the CND sites and the donor is not. In another embodiment, the donor is nullisomic for a CND site and the recipient is not. The donor need not be genotyped as there is a 1 in 2 chance (50% probability) that if a recipient has a given CND site, the donor will not or vice versa. Table 3 is an example of a panel of suitable CND sites useful in the practice of the present assay. The CNDs in Table 3 are referred to as "CND_0X" where X is a numeral from 1 to 10. These correlate to a CNP ID in Table 2 via their CNP_id. in Table 3.

Hence, the subject specification teaches a method for determining the status of donor tissue transplanted into a recipient, the method comprising screening a sample from the recipient for the presence or absence of circulatory nucleic acids which have or do not have a CND polymorphism which indicates it is donor nucleic acids wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

Further taught here is a method for determining the status of donor tissue transplanted into a recipient, the method comprising screening circulatory nucleic acids in sample from the recipient for the presence of CNV polymorphism selected from a panel of polymorphisms wherein the recipient's nucleic acids comprise the presence or absence of at least one polymorphism not shared by the donor wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

In an embodiment, the present specification enables a method for determining the status of donor tissue transplanted into a recipient, the method comprising selecting a panel of from 1 to 200 oligonucleotide primer pairs which target from 1 to 200 known CNV polymorphisms, screening a sample from the recipient for the presence of nucleic acids with the presence of circulatory nucleic acids with the from 1 to 200 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of apoptosis of cellular damage of the transplanted tissue and the absence of non-recipient nucleic acids or a level of non-recipient nucleic acids relative to a control is indicative of no cellular damage or cellular damage to an acceptable level.

In an embodiment, the present specification enables a method for determining the status of donor tissue transplanted into a recipient, the method comprising selecting a panel of from 1 to 100 oligonucleotide primer pairs which target from 1 to 100 known CNV polymorphisms, screening a sample from the recipient for the presence of nucleic acids with the presence of circulatory nucleic acids with the from 1 to 100 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of apoptosis of cellular damage of the transplanted tissue and the absence of non-recipient nucleic acids or a level of non-recipient nucleic acids relative to a control is indicative of no cellular damage or cellular damage to an acceptable level.

In an embodiment, the present specification enables a method for determining the status of donor tissue transplanted into a recipient, the method comprising selecting a panel of from 1 to 10 oligonucleotide primer pairs which target from 1 to 10 known CNV polymorphisms, screening a sample from the recipient for the presence of nucleic acids with the presence of circulatory nucleic acids with the from 1 to 10 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of apoptosis of cellular damage of the transplanted tissue and the absence of non-recipient nucleic acids or a level of non-recipient nucleic acids relative to a control is indicative of no cellular damage or cellular damage to an acceptable level.

In an embodiment, the CNV polymorphism panel is selected from the list in Table 2 wherein the recipient is characterized by having the null genotype for at least one CNV region in the panel wherein the presence of nucleic acids characterized by not having the null genotype for at least one CNV region in the panel indicates the nucleic acids are non-recipient nucleic acids wherein the presence of donor (non-recipient) nucleic acids is indicative of cellular damage of the transplanted tissue and the absence of donor (non-recipient) nucleic acids or a level of non-recipient nucleic acids relative to a control is indicative of no cellular damage or cellular damage to an acceptable level.

An example of a panel of CNVs is the CND panel set forth in Table 3.

Accordingly, the present disclosure teaches a method for determining the status of donor organ transplanted into a recipient, the method comprising screening a sample from the recipient for the presence or absence of circulatory nucleic acids which have a CNV polymorphism selected from the list in Table 2 wherein nucleic acids characterized by not having the null genotype for at least one CNV region in the panel indicates nucleic acids are donor nucleic acids wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

In an embodiment, the present disclosure teaches a method for determining the status of donor organ transplanted into a recipient, the method comprising screening a sample from the recipient for the presence or absence of circulatory nucleic acids which have a CND polymorphism selected from the list in Table 3 wherein nucleic acids characterized by not having the null genotype for at least one CND region in the panel indicates nucleic acids are donor nucleic acids wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

The present specification enables a method for determining the status of donor organ transplanted into a recipient, the method comprising selecting a panel of from 1 to 200 oligonucleotide primer pairs which target from 1 to 200 known CNV polymorphisms selected from the list set forth in Table 2, screening a sample from the recipient for the presence of nucleic acids with the presence of circulatory nucleic acids with the from 1 to 200 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of cellular damage of the transplanted tissue and the absence of non-recipient nucleic acids or a level of non-recipient nucleic acids relative to a control is indicative of no cellular damage or cellular damage to an acceptable level.

The present specification is further instructional for a method for determining the status of donor organ transplanted into a recipient, the method comprising screening circulatory nucleic acids in sample from the recipient for the presence of CNV polymorphism selected from a panel of polymorphisms as set forth in Table 2 wherein the recipient's nucleic acids comprise the presence or absence of at least one polymorphism not shared by the donor wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

In an embodiment, the tissue is an organ selected from the list consisting of a kidney, heart, lung, pancreatic islet, liver and intestine.

The present disclosure also teaches a method for determining the status of a donor kidney transplanted into a recipient, the method comprising screening a sample from the recipient for the presence or absence of circulatory nucleic acids which have a CNV polymorphism selected from the list set forth in Table 2 wherein the presence of nucleic acids not having the null genotype for at least one CNV region in the panel indicates the nucleic acids are donor nucleic acids wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

The present specification enables a method for determining the status of donor tissue transplanted into a recipient, the method comprising selecting a panel of from 1 to 50 oligonucleotide primer pairs which target from 1 to 200 known CNV polymorphisms such as selected from the list set forth in Table 2, screening a sample from the recipient for the presence of circulatory nucleic acids with the presence of nucleic acids with the from 1 to 200 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

The present specification is further instructional for a method for determining the status of a donor kidney transplanted into a recipient, the method comprising screening circulatory nucleic acids in sample from the recipient for the presence of CNV polymorphism selected from a panel of polymorphisms as set forth in Table 2 wherein the presence of nucleic acids not having the null genotype for at least one CNV region in the panel indicates the nucleic acids are donor nucleic acids wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

The biological sample includes a body fluid such as plasma, whole blood, serum, urine, pus, respiratory fluid, lymph fluid, feces, bile, saliva, sputum, semen, vaginal flow, cerebrospinal fluid, brain fluid, ascites, milk, secretions from the genitourinary tract and a lavage of a tissue or organ (e.g. a lung).

In an embodiment, the sample is blood plasma.

In an embodiment, the CNV is a CND. Examples of CNDs are listed in Table 3.

The present disclosure teaches a method for determining the status of donor tissue transplanted into a recipient, the method comprising screening a blood plasma sample from the recipient for the presence or absence of nucleic acids which have a CNV polymorphism including a CND polymorphism such as a CND listed in Table 2 or 3 which indicates it is donor nucleic acids wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

An example of an acceptable level of donor nucleic acids is a level which enables the health of the patent to be maintained.

Taught herein is a method for determining the status of donor tissue transplanted into a recipient, the method comprising selecting a panel of from 1 to 200 oligonucleotide primer pairs which target from 1 to 200 known CNV polymorphisms such as a CNDs listed in Table 2 or 3, screening a blood plasma from the recipient for the presence of nucleic acids with the presence of nucleic acids with the from 1 to 200 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

The present specification is further instructional for a method for determining the status of donor tissue transplanted into a recipient, the method comprising screening nucleic acids in blood plasma from the recipient for the presence of CNV polymorphism such as a CND polymorphism selected from a panel of polymorphisms such as listed in Table 2 or 3 wherein the recipient's nucleic acids comprise the presence or absence of at least one polymorphism not shared by the donor wherein the presence of donor nucleic acids is indicative of apoptosis of cellular damage of the transplanted tissue and the absence of donor nucleic acids or a level of donor nucleic acids relative to a control is indicative of no cellular damage or cellular damage to an acceptable level.

In an embodiment, the present disclosure teaches a method for determining the status of donor organ transplanted into a recipient the donor organ selected from the list consisting of a kidney, heart, lung, pancreatic islet, liver and intestine, the method comprising screening a blood plasma from the recipient for the presence or absence of nucleic acids which have a CNV polymorphism which indicates it is from the transplanted tissue of the donor wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

In an embodiment, the present specification enables a method for determining the status of donor organ transplanted into a recipient the donor organ selected from the list consisting of a kidney, heart, lung, pancreatic islet, liver and intestine, the method comprising selecting a panel of from 1 to 200 oligonucleotide primer pairs which target from 1 to 200 known CNV polymorphisms, screening a blood plasma sample from the recipient for the presence of nucleic acids with the presence of nucleic acids with the from 1 to 200 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

In an embodiment, the present specification enables a method for determining the status of donor organ transplanted into a recipient the donor organ selected from the list consisting of a kidney, heart, lung, pancreatic islet, liver and intestine, the method comprising selecting a panel of from 1 to 100 oligonucleotide primer pairs which target from 1 to 100 known CNV polymorphisms, screening a blood plasma sample from the recipient for the presence of nucleic acids with the presence of nucleic acids with the from 1 to 100 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

In an embodiment, the present specification enables a method for determining the status of donor organ transplanted into a recipient the donor organ selected from the list consisting of a kidney, heart, lung, pancreatic islet, liver and intestine, the method comprising selecting a panel of from 1 to 10 oligonucleotide primer pairs which target from 1 to 10 known CNV polymorphisms, screening a blood plasma sample from the recipient for the presence of nucleic acids with the presence of nucleic acids with the from 1 to 10 oligonucleotide primer pairs wherein the recipient nucleic acids are characterized as having or not having at least one of the known CNV polymorphisms from the panel and the donor nucleic acids are distinguished from the recipient on the basis of having or not having the polymorphism shared by the recipient, wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

The CNVs include CNDs such as those listed in Table 2 as exemplified in Table 3.

The present specification is further instructional for a method for determining the status of donor organ transplanted into a recipient, the donor organ selected from the list consisting of a kidney, heart, lung, pancreatic islet, liver and intestine, the method comprising screening nucleic acids in blood plasma sample from the recipient for the presence of CNV polymorphism selected from a panel of polymorphisms selected from the list in Table 2 wherein the recipient's nucleic acids comprise the presence or absence of at least one polymorphism not shared by the donor wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

In an embodiment, the tissue is an organ is a kidney.

Hence, the present disclosure teaches a method for determining the status of a donor kidney transplanted into a recipient, the method comprising screening a blood plasma from the recipient for the presence or absence of nucleic acids which have a CNV polymorphism selected from the list in Table 2 which indicates it is donor nucleic acids wherein the presence of donor nucleic acids is indicative of cellular damage of the transplanted tissue and the absence of donor nucleic acids or a level of donor nucleic acids relative to a control is indicative of no cellular damage or cellular damage to an acceptable level.

Blood sampling may be accomplished by any technique known in the art such as via syringe, vacuum suction device, pin prick and the like. A blood sample may be further treated or processed such as to concentrate the presence of nucleic acids to remove high abundance molecules, to reduce coagulation, to reduce thrombolysis, to adjust the pH or osmolality or to stabilize the fluid. The blood sample, if treated appropriately, including its storage, may be maintained and assayed from less than one hour to 24 hours to 2 weeks after collection. Alternatively, it is assayed immediately or within a 24 hour period from collection.

The nucleic acids are generally genomic DNA but may also be mRNA or other RNA species. The RNA may be screened for directly or after conversion to DNA such as cDNA.

Methods and kits are taught herein to readily screen a patient following a transplantation procedure. A panel of primers which detail common CNV polymorphisms is used. An example is set forth in Table 2 in relation to CNV polymorphisms. In an embodiment, recipients have the null genotype (i.e. zero copies) for at least one CND site in the panel. Table 3 is an example of a CND subset of CNVs listed in Table 2.

The recipient may express all or some of the CNV polymorphisms. The donor does not have to be genotyped with respect to CNV polymorphisms since any nucleic acids which are not the recipients nucleic acids are presumed to be the donor's nucleic acids. The method enabled herein provides a reliable approach to monitor the success or otherwise of a transplantation procedure and/or a method of treatment to mitigate rejection or other form of tissue injury.

Conveniently, the CNV genotype of fluid nucleic acids is determined by an amplification reaction, such as digital or real time PCR followed by gel electrophoresin, nucleotide sequencing, expression of reporter molecules (Gonzalez et al. (2005) *Environ. Michrobiol.* 7(7):1024-1028; DeLa Vega et al. (2005) *Mutation Research* 573:111-135; Livak et al. (1995) *Nature Genetics* 9:341-342).

Amplification reactions useful in the practice of the present method include quantitative PCR (q-PCR), quantitative fluorescent PCR (qf-PCR), multiplex fluorescent PCR (MF-PCR), real time PCR (RT-PCR), single cell PCR, restriction fragment length PCR (PCR-RFLP), PCR-RFLP/RT-PCR-RFLP, hot start PCR, nested PCR, in situ polonony PCR, in situ rolling circle amplification, bridge PCR, picotiter PCR and emulsion PCR. Other amplification methods include selective amplification of target polynucleotide sequences, consensus sequence primed PCR (CP-PCR), arbitrarily primed PCR (AP-PCR), degenerate oligonucleotide-primer PCR (DOP-PCR) and nucleic acid based sequence amplification (NAB SA).

Following amplification, the CNV genotype is determined such as by electrophoresis which includes capillary, capillary zone, capillary isoelectric focusing and capillary gel electrophoresis as well as capillary electrochromatography, micellar electrokinetic capillary chromatography and transient isotachophoresis by use of arrays, beads, gas chromatography, supercritical fluid chromatography, liquid chromatography (which encompasses partition, adsorption, ion exchange, size exclusion, thin-layer and affinity chromatography). Other techniques include comparative genomic hybridization, microarrays, bead arrays and high throughput genotyping such as with the use of a molecular inversion probe.

Also enabled herein are reagents and kits for screening for or quantitating donor-derived nucleic acids. The subject reagents and kits may vary in form and control. Reagents of interest include reagents specifically designed for (i) genotyping nucleic acid from a recipient; (ii) identification of marker profiles; and (ii) detection and/or quantitation of one or more nucleic acids from a transplant donor in a sample obtained from a transplant recipient.

One type of such reagents are one or more probes or an array of probes to genotype and/or to detect and/or to quantitate one or more nucleic acids. A variety of different array formats are known in the art, with a wide variety of different probe structures, substrate compositions and attachment technologies. In an example, the CNV polymorphisms listed in Table 2 are screened by a panel of oligonucleotide primers and/or probes. In an example, CND polymorphism listed in Table 3 are screened by a panel of oligonucleotide primers and/or probes.

The kits herein may include arrays or other solid phase platforms. Such kits may additionally comprise one or more therapeutic agents. The kit may further comprise a software package for data analysis, which may include reference profiles for comparison with the test profile.

The kits may comprise reagents such as buffers and $H_2O$ or other excipients. The kits may comprise reagents necessary to perform nucleic acid extraction and/or nucleic acid detection using the methods described herein such as PCR and sequencing.

Such kits may also include information, such as scientific literature references, package insert materials, diagnostic trial results, and/or summaries of these and the like, which indicate or establish the activities and/or advantages of the diagnostic assay indicative of the presence of donor nucleic acids in a body sample. Such kits may also include instructions to access a database. Such information may include results of pre-determined trials and controls based on human or animal diagnostic trials. Kits described herein can be provided, marketed and/or promoted to health providers, including physicians, nurses, pharmacists, formulary officials, and the like. Kits may also, in some embodiments, be marketed directly to the consumer. The latter is particularly useful for home care and personalized medicine.

Any of the methods above can be performed by a computer program product that comprises a computer executable logic that is recorded on a computer readable medium. For example, the computer program can execute some or all of the following functions: (i) controlling isolation of nucleic acids from a sample, (ii) pre-amplifying nucleic acids from the sample, (iii) amplifying, sequencing or arraying specific polymorphic regions in the sample, (iv) identifying and quantifying a CNV marker profile in the sample, (v) comparing data on the CNV marker profile detected from the sample with a predetermined threshold, (vi) determining a transplant status or outcome, (vi) declaring normal or abnormal transplant status or outcome. In an embodiment, the computer executable logic can analyze data on the detection and quantity of CND polymorphisms.

The computer executable logic can work in any computer that may be any of a variety of types of general-purpose computers such as a personal computer, network server, workstation, or other computer platform including handheld and portable devices. In an embodiment, a computer program product is described comprising a computer usable medium having the computer executable logic (computer software program, including program code) stored therein. The computer executable logic can be executed by a processor, causing the processor to perform functions described herein. In an other embodiment, some functions are implemented primarily in hardware using, for example, a hardware state machine. Implementation of the hardware state machine so as to perform the functions described herein will be apparent to those skilled in the relevant arts.

The program can provide a method of evaluating a transplant status or outcome in a transplant recipient by accessing data that reflects the genotyping of the transplant recipient and/or the presence or absence of one or more nucleic acids from the transplant donor in the circulation of the transplant patient post-transplantation.

In an embodiment, the computer executing the computer logic herein described may also include a digital input device such as a scanner. The digital input device can provide information on a nucleic acid, e.g. CNV (e.g. CND) presence or quantity. For example, a scanner herein described can provide an image of the CNV (e.g. CND) according to subject assay method. For instance, a scanner can provide an image by detecting fluorescent, radioactive, or other emission; by detecting transmitted, reflected, or scattered radiation; by detecting electromagnetic properties or other characteristics; or by other techniques. The data detected are typically stored in a memory device in the form of a data file. In an embodiment, a scanner may identify one or more labeled targets. For instance, a first CNV polymorphism may be labeled with a first dye that fluoresces at a particular characteristic frequency, or narrow band of frequencies, in response to an excitation source of a particular frequency. A second CNV polymorphism may be labeled with a second dye that fluoresces at a different characteristic frequency. The excitation sources for the second dye may, but need not, have a different excitation frequency than the source that excites the first dye, e.g. the excitation sources could be the same, or different, lasers.

In an embodiment, the subject disclosure teaches a computer readable medium comprising a set of instructions recorded thereon to cause a computer to perform the steps of (i) receiving data from one or more nucleic acids detected in a sample from a subject who has received transplant from a donor, wherein the one or more nucleic acids are nucleic acids not from the recipient (i.e. the one or more nucleic acids are from the donor transplant) and wherein the one or more nucleic acids from the donor are identified based on a predetermined CNV marker profile (e.g. CNV profile listed in Table 2); and (ii) diagnosing or predicting transplant status or outcome based on the presence or absence of the one or more nucleic acids.

The present disclosure further enables a transplantation protocol for transplanting tissue from a donor to a recipient, the protocol comprising transplanting the tissue and then monitoring a sample from the recipient for the presence of nucleic acids which are not the recipients wherein if donor nucleic acids are detected, the recipient is subjected to immunosuppression therapy or if the patient is on immunosuppression therapy, the therapy is altered.

Another aspect taught herein is the use of a panel of CNVs which identify a nucleic acid as being of recipient origin or non-recipient origin in the manufacture of a diagnostic assay to detect the status of transplanted tissue in the recipient.

The subject disclosure further teaches an assay to monitor the balance between immunosuppression and tissue damage such as due to rejection or pharmaceutical cytotoxicity. Hence, the subject disclosure teaches a method of treating a subject who has undergone a transplantation procedure by monitoring for changes in the levels of non-recipient nucleic acids. Such changes may be relative to a control. The control includes pre-transplantation levels of free recipient nucleic acids or a change in the ratio of total nucleic acids to non-recipient nucleic acids.

Whilst Table 2 provides a list of CNV polymorphisms, the present method extends to other known CNV polymorphisms such as those described by Conrad et al. (2010) supra and McCarroll et al. (2008) supra.

Aspects contemplated herein are further described by the following non-limiting Examples.

Example 1

Development of a CNV-Deletion Genotyping Panel to Distinguish Recipient from Donor Plasma DNA A panel of CNV deletions is selected which is expected to have approximate null frequencies of 40-50% in the general population. This is done by in silico analysis of public data (Conrad et al. (2010) supra; McCarroll et al. (2008) supra). These CNV regions are polymorphic and have no intrinsic clinical significance. CNV selection and frequency calculations are performed as follows: The HapMap data set includes trio-data for each CNV. For frequency calculations, only singleton and parental samples are included. CNVs with only 0, 1 and 2 copy genotypes are selected for analysis (i.e. CNVs of more than 2 copy and Chromosomes X and Y CNVs are excluded). For each selected CNV, frequencies of 0, 1 and 2 copy genotypes are calculated. CNVs in the form of CNDs overlapping with segmental duplications were excluded. CNVs with 0.4-0.5 null copy frequency and less than 3 kb in size were selected from Table 2. The list in Table 2 should be read in conjunction with, and includes, other known CNVs such as those defined in Conrad et al. (2010) supra; McCarroll et al. (2008) supra. An example is the CNVs listed in Table 3.

TABLE 2

| | | | | | | | |
|---|---|---|---|---|---|---|---|
| | | Copy Number Variant Polymorphisms | | | | | |
| CNP ID | Chr | Start (hg18) | End (hg18) | Size (bp) | 0 Copy frequency | 1 Copy frequency | 2 Copy frequency |
| CNVR358.1 | chr1 | 150,822,234 | 150,856,715 | 34481 | 0.393 | 0.459 | 0.148 |
| CNVR217.1 | chr1 | 72,538,870 | 72,584,557 | 45687 | 0.393 | 0.459 | 0.148 |
| CNVR483.1 | chr1 | 205,359,125 | 205,359,831 | 706 | 0.459 | 0.426 | 0.115 |
| CNVR451_full | chr1 | 192,716,897 | 192,721,360 | 4463 | 0.459 | 0.418 | 0.107 |
| CNVR376.1 | chr1 | 157,134,152 | 157,136,674 | 2522 | 0.508 | 0.418 | 0.074 |
| CNVR381.1 | chr1 | 157,915,386 | 157,916,253 | 867 | 0.582 | 0.344 | 0.049 |
| 88 | chr1 | 110,025,907 | 110,044,476 | 18569 | 0.583 | 0.350 | 0.067 |
| CNVR431.1 | chr1 | 185,731,458 | 185,733,106 | 1648 | 0.598 | 0.320 | 0.041 |
| 262 | chr2 | 97,507,179 | 97,528,142 | 20963 | 0.367 | 0.450 | 0.167 |
| CNVR1138.2 | chr2 | 219,761,436 | 219,762,572 | 1136 | 0.385 | 0.410 | 0.180 |
| CNVR1138.3 | chr2 | 219,760,351 | 219,762,572 | 2221 | 0.385 | 0.418 | 0.164 |
| CNVR966.1 | chr2 | 126,159,644 | 126,168,438 | 8794 | 0.393 | 0.418 | 0.164 |
| CNVR1037.1 | chr2 | 159,668,040 | 159,669,209 | 1169 | 0.492 | 0.418 | 0.066 |
| CNVR952.1 | chr2 | 121,513,996 | 121,515,257 | 1261 | 0.516 | 0.352 | 0.098 |
| CNVR801_full | chr2 | 54,419,132 | 54,420,976 | 1844 | 0.574 | 0.361 | 0.041 |
| CNVR842.1 | chr2 | 76,627,234 | 76,628,943 | 1709 | 0.582 | 0.320 | 0.074 |
| CNVR1041_full | chr2 | 162,039,479 | 162,042,198 | 2719 | 0.672 | 0.270 | 0.033 |
| CNVR1058.1 | chr2 | 176,973,956 | 176,980,168 | 6212 | 0.672 | 0.254 | 0.049 |
| CNVR894.2 | chr2 | 101,419,843 | 101,420,750 | 907 | 0.680 | 0.180 | 0.008 |
| CNVR1648.2 | chr3 | 180,032,900 | 180,033,574 | 674 | 0.352 | 0.492 | 0.156 |
| CNVR1438_full | chr3 | 80,144,512 | 80,147,226 | 2714 | 0.377 | 0.484 | 0.139 |
| CNVR1576.1 | chr3 | 147,867,879 | 147,873,031 | 5152 | 0.426 | 0.459 | 0.115 |
| CNVR1419.1 | chr3 | 68,822,189 | 68,830,557 | 8368 | 0.426 | 0.393 | 0.180 |
| CNVR1685.1 | chr3 | 194,358,041 | 194,368,093 | 10052 | 0.443 | 0.443 | 0.115 |
| CNVR1610.1 | chr3 | 164,247,638 | 164,251,756 | 4118 | 0.508 | 0.426 | 0.066 |
| CNVR1341.1 | chr3 | 32,077,088 | 32,082,966 | 5878 | 0.516 | 0.361 | 0.107 |
| CNVR1464.1 | chr3 | 100,381,786 | 100,385,095 | 3309 | 0.656 | 0.295 | 0.041 |
| CNVR2196.1 | chr4 | 182,293,552 | 182,294,187 | 635 | 0.352 | 0.443 | 0.148 |
| CNVR1894.1 | chr4 | 39,701,722 | 39,702,524 | 802 | 0.361 | 0.516 | 0.123 |
| CNVR2221_full | chr4 | 187,330,507 | 187,348,434 | 17927 | 0.361 | 0.492 | 0.123 |
| CNVR1937.1 | chr4 | 61,621,762 | 61,624,843 | 3081 | 0.369 | 0.525 | 0.107 |
| CNVR1935_full | chr4 | 61,012,725 | 61,017,305 | 4580 | 0.492 | 0.434 | 0.074 |
| CNVR1819.6 | chr4 | 9,783,252 | 9,843,664 | 60412 | 0.508 | 0.410 | 0.082 |
| CNVR2172_full | chr4 | 173,661,594 | 173,670,645 | 9051 | 0.525 | 0.434 | 0.016 |
| CNVR2168_full | chr4 | 172,610,978 | 172,616,208 | 5230 | 0.557 | 0.361 | 0.025 |
| 726 | chr4 | 173,661,522 | 173,665,218 | 3696 | 0.567 | 0.350 | 0.067 |
| CNVR2613_full | chr5 | 135,143,151 | 135,148,760 | 5609 | 0.377 | 0.484 | 0.139 |
| CNVR2535_full | chr5 | 98,373,056 | 98,375,260 | 2204 | 0.402 | 0.410 | 0.189 |
| CNVR2344_full | chr5 | 10,326,006 | 10,327,951 | 1945 | 0.467 | 0.385 | 0.115 |
| CNVR2469.1 | chr5 | 57,359,283 | 57,369,499 | 10216 | 0.615 | 0.361 | 0.025 |
| CNVR2304.1 | chr5 | 1,977,604 | 1,978,111 | 507 | 0.672 | 0.328 | 0.000 |
| 896 | chr5 | 177,160,157 | 177,165,211 | 5054 | 0.683 | 0.300 | 0.017 |
| CNVR2939.3 | chr6 | 65,405,092 | 65,405,828 | 736 | 0.369 | 0.426 | 0.139 |
| CNVR2939.2 | chr6 | 65,401,412 | 65,406,139 | 4727 | 0.369 | 0.475 | 0.156 |
| CNVR2799.1 | chr6 | 18,510,099 | 18,510,860 | 761 | 0.393 | 0.426 | 0.148 |
| CNVR3004.1 | chr6 | 95,250,114 | 95,251,113 | 999 | 0.393 | 0.459 | 0.123 |
| CNVR2906.1 | chr6 | 54,036,723 | 54,042,793 | 6070 | 0.451 | 0.475 | 0.066 |
| CNVR2972_full | chr6 | 77,154,212 | 77,160,412 | 6200 | 0.459 | 0.443 | 0.090 |
| CNVR2859_full | chr6 | 35,734,415 | 35,737,723 | 3308 | 0.467 | 0.443 | 0.082 |
| 933 | chr6 | 32,539,530 | 32,681,749 | 142219 | 0.550 | 0.383 | 0.067 |
| CNVR3009.1 | chr6 | 100,141,275 | 100,141,994 | 719 | 0.623 | 0.377 | 0.000 |
| CNVR3472_full | chr7 | 81,279,416 | 81,280,521 | 1105 | 0.377 | 0.467 | 0.156 |
| CNVR3319.1 | chr7 | 24,004,755 | 24,006,584 | 1829 | 0.434 | 0.344 | 0.139 |
| CNVR3495.1 | chr7 | 93,379,735 | 93,380,461 | 726 | 0.443 | 0.410 | 0.148 |
| 1103 | chr7 | 70,058,925 | 70,064,077 | 5152 | 0.450 | 0.483 | 0.067 |
| CNVR3451.1 | chr7 | 73,467,042 | 73,469,172 | 2130 | 0.549 | 0.328 | 0.123 |
| CNVR3609.1 | chr7 | 147,704,059 | 147,707,263 | 3204 | 0.656 | 0.311 | 0.033 |
| CNVR3753_full | chr8 | 4,110,308 | 4,112,335 | 2027 | 0.426 | 0.426 | 0.131 |
| CNVR3935.1 | chr8 | 75,525,410 | 75,529,549 | 4139 | 0.451 | 0.369 | 0.172 |
| CNVR4014.1 | chr8 | 112,363,260 | 112,365,469 | 2209 | 0.500 | 0.410 | 0.082 |
| CNVR3831.1 | chr8 | 25,122,647 | 25,126,577 | 3930 | 0.598 | 0.328 | 0.049 |
| CNVR3689.1 | chr8 | 584,449 | 589,454 | 5005 | 0.689 | 0.262 | 0.041 |
| CNVR4250.1 | chr9 | 36,352,611 | 36,353,818 | 1207 | 0.369 | 0.508 | 0.115 |
| CNVR4331.1 | chr9 | 70,927,946 | 70,933,190 | 5244 | 0.443 | 0.467 | 0.082 |
| CNVR4374.1 | chr9 | 88,344,772 | 88,345,596 | 824 | 0.557 | 0.361 | 0.074 |
| CNVR4203.1 | chr9 | 17,900,038 | 17,901,633 | 1595 | 0.598 | 0.352 | 0.025 |
| CNVR4332.1 | chr9 | 71,085,050 | 71,086,301 | 1251 | 0.631 | 0.328 | 0.025 |
| CNVR4841.1 | chr10 | 89,265,522 | 89,266,538 | 1016 | 0.377 | 0.459 | 0.156 |
| CNVR4665.1 | chr10 | 27,039,121 | 27,041,860 | 2739 | 0.377 | 0.410 | 0.213 |
| CNVR4886.1 | chr10 | 108,020,303 | 108,022,518 | 2215 | 0.410 | 0.418 | 0.172 |
| CNVR4596.1 | chr10 | 4,698,559 | 4,700,493 | 1934 | 0.607 | 0.311 | 0.082 |
| CNVR4906.1 | chr10 | 122,216,913 | 122,218,702 | 1789 | 0.664 | 0.270 | 0.057 |
| 1730 | chr11 | 54,458,221 | 54,514,519 | 56298 | 0.433 | 0.367 | 0.100 |
| CNVR5122.1 | chr11 | 28,963,726 | 28,969,302 | 5576 | 0.434 | 0.434 | 0.115 |
| CNVR5294.1 | chr11 | 103,772,866 | 103,778,468 | 5602 | 0.475 | 0.369 | 0.148 |

TABLE 2-continued

| | | Start | End | Size | 0 Copy | 1 Copy | 2 Copy |
| CNP ID | Chr | (hg18) | (hg18) | (bp) | frequency | frequency | frequency |
|---|---|---|---|---|---|---|---|
| CNVR5429.1 | chr12 | 9,524,006 | 9,626,453 | 102447 | 0.393 | 0.402 | 0.139 |
| CNVR5853_full | chr13 | 38,831,627 | 38,833,387 | 1760 | 0.385 | 0.451 | 0.148 |
| CNVR5923.1 | chr13 | 71,743,783 | 71,744,892 | 1109 | 0.402 | 0.533 | 0.041 |
| CNVR5850.1 | chr13 | 37,955,318 | 37,958,191 | 2873 | 0.426 | 0.434 | 0.139 |
| CNVR5871.1 | chr13 | 49,967,347 | 49,973,131 | 5784 | 0.590 | 0.361 | 0.033 |
| CNVR6133.1 | chr14 | 39,679,595 | 39,687,469 | 7874 | 0.352 | 0.475 | 0.156 |
| CNVR6211.1 | chr14 | 81,568,879 | 81,573,106 | 4227 | 0.385 | 0.377 | 0.189 |
| CNVR6084.1 | chr14 | 21,951,540 | 21,952,070 | 530 | 0.451 | 0.418 | 0.107 |
| CNVR6074_full | chr14 | 19,621,390 | 19,625,018 | 3628 | 0.582 | 0.344 | 0.057 |
| CNVR6357.1 | chr15 | 37,531,690 | 37,532,136 | 446 | 0.508 | 0.410 | 0.066 |
| CNVR6540.1 | chr15 | 97,392,250 | 97,392,985 | 735 | 0.508 | 0.426 | 0.057 |
| CNVR6670.1 | chr16 | 22,955,370 | 22,957,061 | 1691 | 0.377 | 0.525 | 0.074 |
| CNVR6676.1 | chr16 | 25,247,611 | 25,250,595 | 2984 | 0.443 | 0.459 | 0.074 |
| CNVR6782.1 | chr16 | 75,096,634 | 75,101,530 | 4896 | 0.443 | 0.443 | 0.098 |
| CNVR7144.1 | chr17 | 53,042,845 | 53,044,836 | 1991 | 0.410 | 0.434 | 0.148 |
| CNVR7096.1 | chr17 | 36,675,163 | 36,685,731 | 10568 | 0.484 | 0.402 | 0.107 |
| CNVR7301.1 | chr18 | 33,560,073 | 33,560,645 | 572 | 0.418 | 0.451 | 0.123 |
| CNVR7344.1 | chr18 | 53,097,735 | 53,099,702 | 1967 | 0.508 | 0.393 | 0.082 |
| CNVR7543.1 | chr19 | 12,555,939 | 12,559,475 | 3536 | 0.475 | 0.402 | 0.057 |
| CNVR7581_full | chr19 | 22,932,698 | 22,934,767 | 2069 | 0.648 | 0.270 | 0.025 |
| 2434 | chr19 | 58,210,563 | 58,244,245 | 33682 | 0.683 | 0.233 | 0.067 |
| 2454 | chr20 | 1,509,580 | 1,541,893 | 32313 | 0.483 | 0.467 | 0.050 |
| CNVR7808.1 | chr20 | 21,234,267 | 21,236,529 | 2262 | 0.516 | 0.418 | 0.066 |
| CNVR7849.1 | chr20 | 41,705,581 | 41,707,310 | 1729 | 0.664 | 0.311 | 0.008 |
| CNVR7796_full | chr20 | 15,657,506 | 15,660,363 | 2857 | 0.672 | 0.279 | 0.033 |
| 2559 | chr22 | 22,613,016 | 22,670,785 | 57769 | 0.383 | 0.467 | 0.150 |
| CNVR8147.1 | chr22 | 33,975,445 | 33,976,472 | 1027 | 0.451 | 0.426 | 0.115 |
| CNVR8114.4 | chr22 | 22,604,143 | 22,607,619 | 3476 | 0.451 | 0.434 | 0.107 |
| CNVR8154.1 | chr22 | 35,473,303 | 35,476,957 | 3654 | 0.566 | 0.352 | 0.074 |

TABLE 3

Copy Number Deletion Polymorphisms

| | | | start | end | SIZE | 0 Copy | 1 Copy | 2 Copy | CNV |
| CND ID | CNP_id | chr | hg18 | hg18 | bp | frequency | frequency | frequency | Info |
|---|---|---|---|---|---|---|---|---|---|
| CND_01 | CNVR376.1 | chr1 | 157,134,152 | 157,136,674 | 2,522 | 0.508 | 0.418 | 0.074 | agenic |
| CND_02 | CNVR7344.1 | chr18 | 53,097,735 | 53,099,702 | 1,967 | 0.508 | 0.393 | 0.082 | agenic |
| CND_03 | CNVR4014.1 | chr8 | 112,363,260 | 112,365,469 | 2,209 | 0.500 | 0.410 | 0.082 | agenic |
| CND_04 | CNVR6084.1 | chr14 | 21,951,540 | 21,952,070 | 530 | 0.451 | 0.418 | 0.107 | Intronic |
| CND_05 | CNVR6676.1 | chr16 | 25,247,611 | 25,250,595 | 2,984 | 0.443 | 0.459 | 0.074 | agenic |
| CND_06 | CNVR3319.1 | chr7 | 24,004,755 | 24,006,584 | 1,829 | 0.434 | 0.344 | 0.139 | agenic |
| CND_07 | CNVR5850.1 | chr13 | 37,955,318 | 37,958,191 | 2,873 | 0.426 | 0.434 | 0.139 | agenic |
| CND_08 | CNVR3753_full | chr8 | 4,110,308 | 4,112,335 | 2,027 | 0.426 | 0.426 | 0.131 | Intronic |
| CND_09 | CNVR7301.1 | chr18 | 33,560,073 | 33,560,645 | 572 | 0.418 | 0.451 | 0.123 | agenic |
| CND_10 | CNVR4886.1 | chr10 | 108,020,303 | 108,022,518 | 2,215 | 0.410 | 0.418 | 0.172 | agenic |

Example 2

Genotyping Recipients Using Simple PCR Assays with Cell-Derived DNA

Figure 1B:
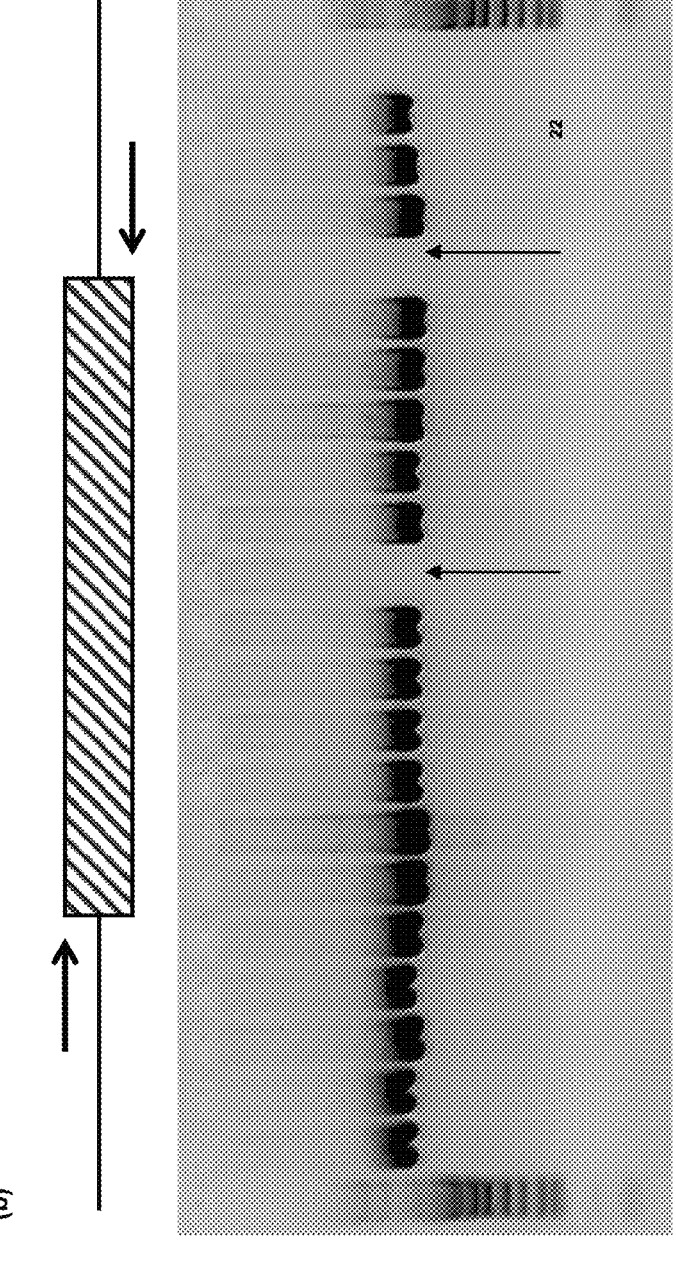
FIG. 1b is a diagrammatic and photographic representation of CND_01 flanking PCR: Lanes 2-22 are the same 21 control samples (19/21 are null or 1 copy; 2/21 are 2 copy wild-type (arrowed); lane 1 and 24—Marker VIII and lane 23—blank.

PCR reactions are designed with primers located within the 10 CNV-deletion regions provided in Table 3 (Example 1) to confirm the expected null frequencies (i.e. no PCR product) using genomic DNA from a group of 21 normal individuals. FIG. 1a shows confirmation of the predicted 40-50% frequency for CND_01, i.e. 12 out of 21 null genotypes. To confirm that the deletions are real rather than PCR failure artefacts, PCR reactions are run with flanking primers. The results are shown for CND_01 (FIG. 1b). These give a precise product shorter than the wild-type confirming all the null deletions detected in (a), the rest being null/wild-type heterozygotes with the exception of two (arrowed) that are wild-type homozygotes (note: the larger, wild-type product is absent as the undeleted CNV is too large to be amplified).

Example 3

Validation of the Genotyping PCRs

The identity of the internal PCR products is proven unequivocally by sequencing the corresponding, shorter flanking PCR products and mapping them back to a genome location using BLAT. In all cases, this was to the correct, unique genome locus.

An advantage of this approach is that there is no need to genotype the donor. Recipient genotype is determined using the leukocyte cell component of the same anti-coagulated blood sample from which plasma is obtained. The assay detects non-self, i.e. donor specific, CNV regions in plasma.

Example 4

CNV-Deletion Genotyping Using Plasma-Derived DNA

Figure 2:
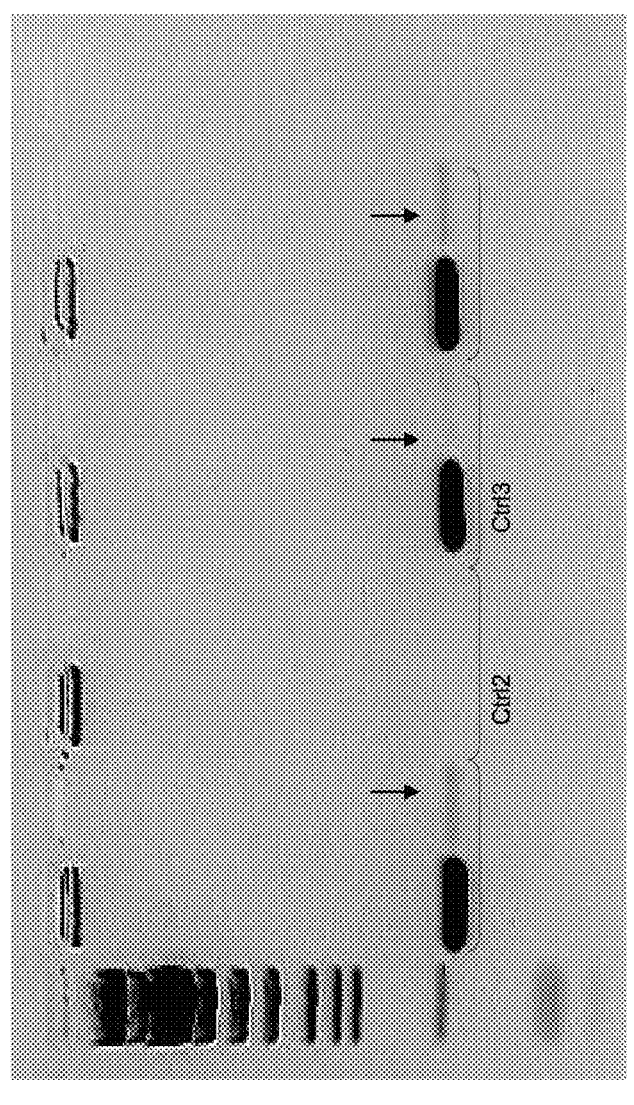
FIG. 2 is a photographic representation of internal PCR on cellular and plasma DNA for CND_02: —For 4 control samples, cellular and plasma DNA sample were tested in alternate lanes (lane 2 to 9). Difference in the band intensity is due to the different amounts of DNA in plasma and cellular sample (Cellular DNA is equivalent to 19000 GE, whereas plasma DNA is equivalent to ~250GE in the reaction).

CNV-deletion (CND) genotyping using plasma DNA is demonstrated. Unlike cell-derived DNA, plasma DNA is degraded into short 400-600 bp fragments. FIG. 2 demonstrates completely concordant CNV-deletion genotyping for 4 individuals (3 heterozygotes/or homozygotes and 1 null) using leukocyte DNA and plasma DNA from the same blood samples, in this case for CND_02 by PCR.

Example 5

Optimization of the CNV-Detection Panel (100-150 Individuals)

In order to optimize the CNV-deletion panel for use in the local population, it is necessary to determine accurately the null frequencies in a larger set of genomic DNA samples (from approximately 100-150 individuals) taking into account differences based on ethnicity. The informativeness of the final panel is likely to be 100% for any one recipient. For very rare recipients who have no 'null' genotypes within the panel, alternative bespoke assays designs can be used based on 'null' genotypes in the donor. In clinical transplantation there is a low level of microchimaerism with donor dendritic cells, in particular. It is not anticipated that the low level of contaminating cells will interfere with establishing the donor DNA profile, as this will not be performed at high sensitivity.

Example 6

Sensitivity of CNV-Deletion Genotyping PCR Using Plasma DNA

Figure 3:
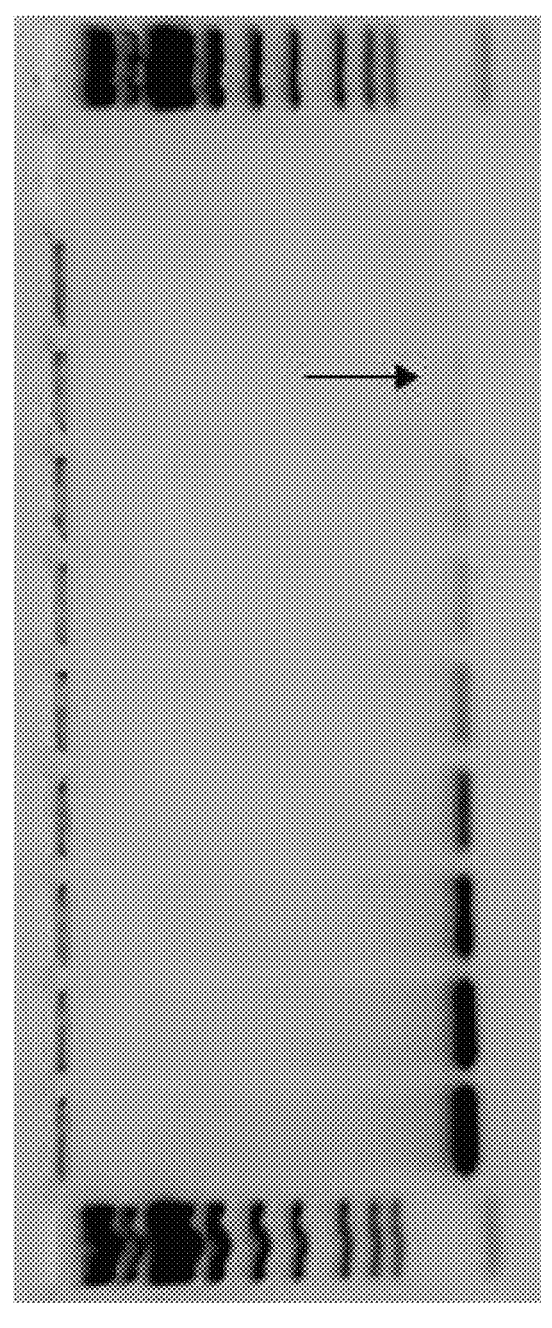
FIG. 3 is a photographic representation of sensitivity of CNV deletion genotyping. The sensitivity was as low as 1%.

An indication of the achievable sensitivity using simple PCR has been obtained from a 'spiking' experiment. A control sample which is heterozygous (i.e. 1 copy) for CND_01 loci is 'spiked' into a nullisomic sample at proportions of 0-100% and run in a simple PCR assay. The results in FIG. 3 show that CND_01 could be detected at proportions as low as 1% (arrowed). Furthermore, q-PCR assays are developed which have sensitivities an order of magnitude more sensitive than 1%.

Example 7

Developing Quantitative PCR (q-PCR) Assays for the Donor CNVs (10 Assays)

Figure 4:
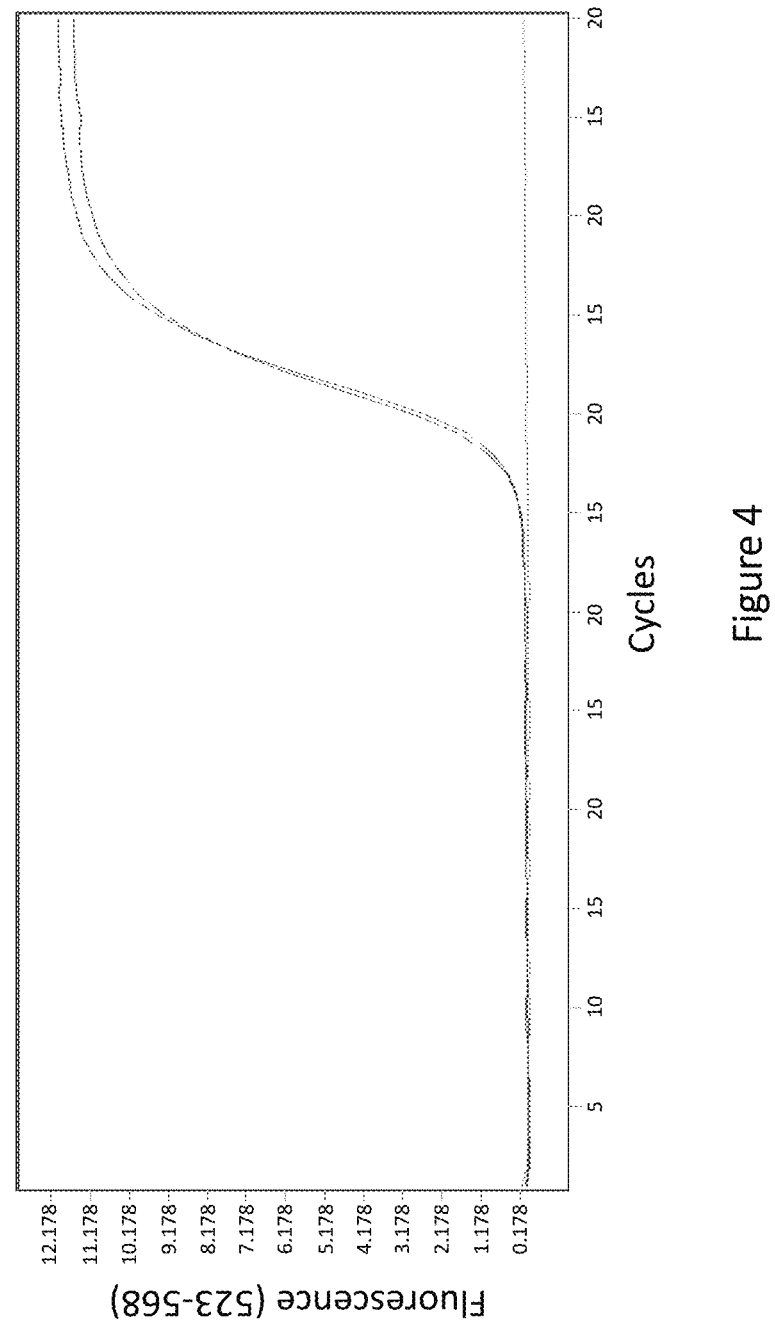
FIG. 4 is a graphical representation of the detection of non-self sex-determining region Y (SRY). DNA in recipient blood plasma using quantitative PCR (q-PCR).

A specific q-PCR assay is developed for each CNV region in the CNV-deletion panel for absolute quantitation of plasma CNV concentrations. This provides very sensitive detection of donor DNA sequences matching the recipient CNV-deletions. An analogous q-PCR assay for sensitive quantitation of SRY in plasma samples from female recipients with an organ transplant from a male donor (FIG. 4). This is a model system for each of the panel CNV regions. q-PCR is performed essentially as previously described (Lo et al. (1998) *Am J Hum Genet* 62(4):768-75). It demonstrates the feasibility of taking this approach for quantitation of low levels of donor-specific DNA sequences in recipient plasma.

As very low concentrations of DNA are assayed using q-PCR, there is a risk of contamination with DNA from other sources (operator or samples). The multiple informative CNV-deletions that are assayed for each recipient-donor pair provides a valuable indicator of any inconsistencies in individual assay results. An additional requirement is that 'no template' controls are included in each qPCR experiment.

Example 8

Sensitivity of qPCR Assays Using Genomic DNA

Figure 5A:
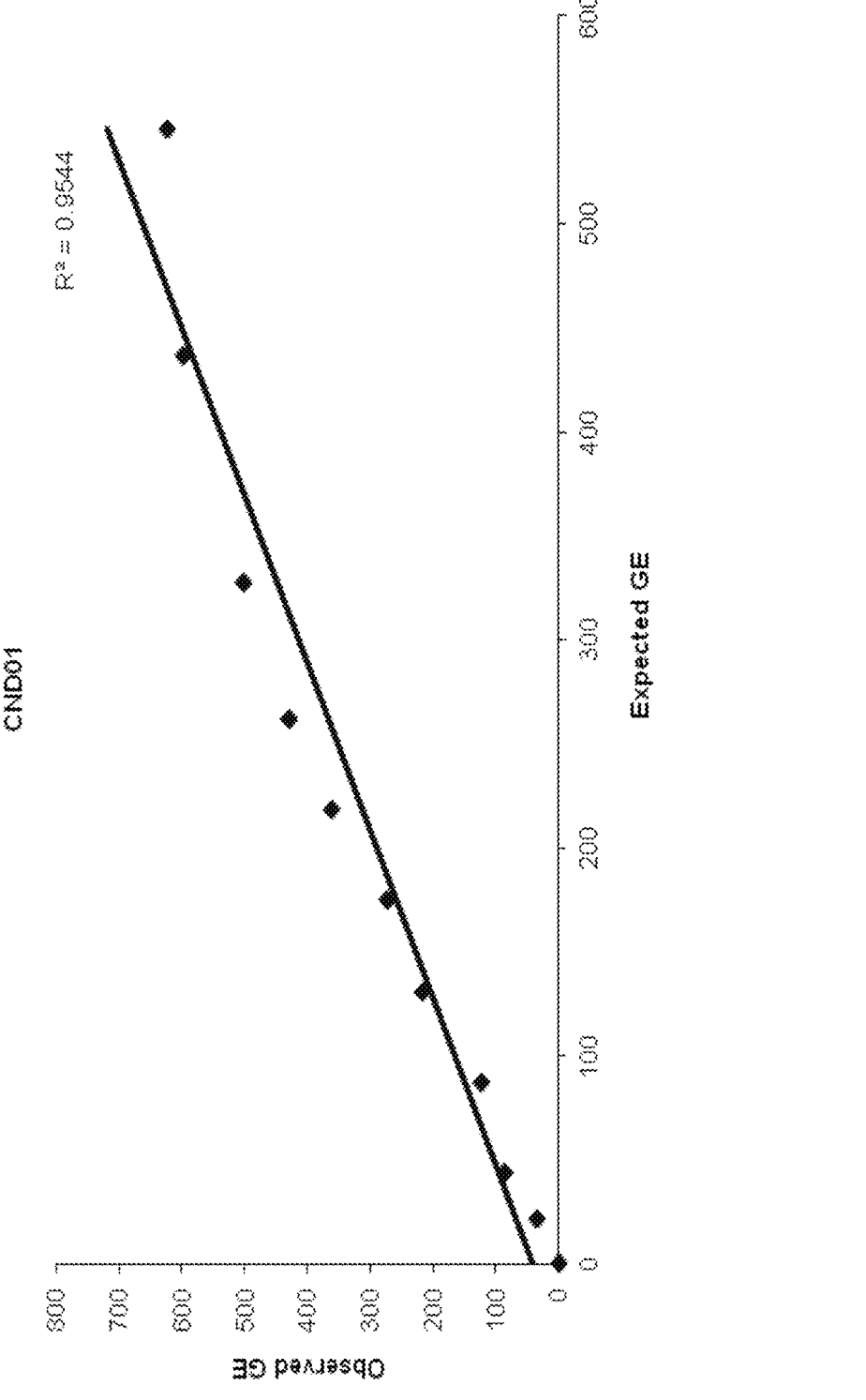
FIGS. 5a through 5c are graphical representations of CND_01, CND_02 and CDN_03 showing accurate, precise and robust measurements of rare DNA.
Figure 5B:
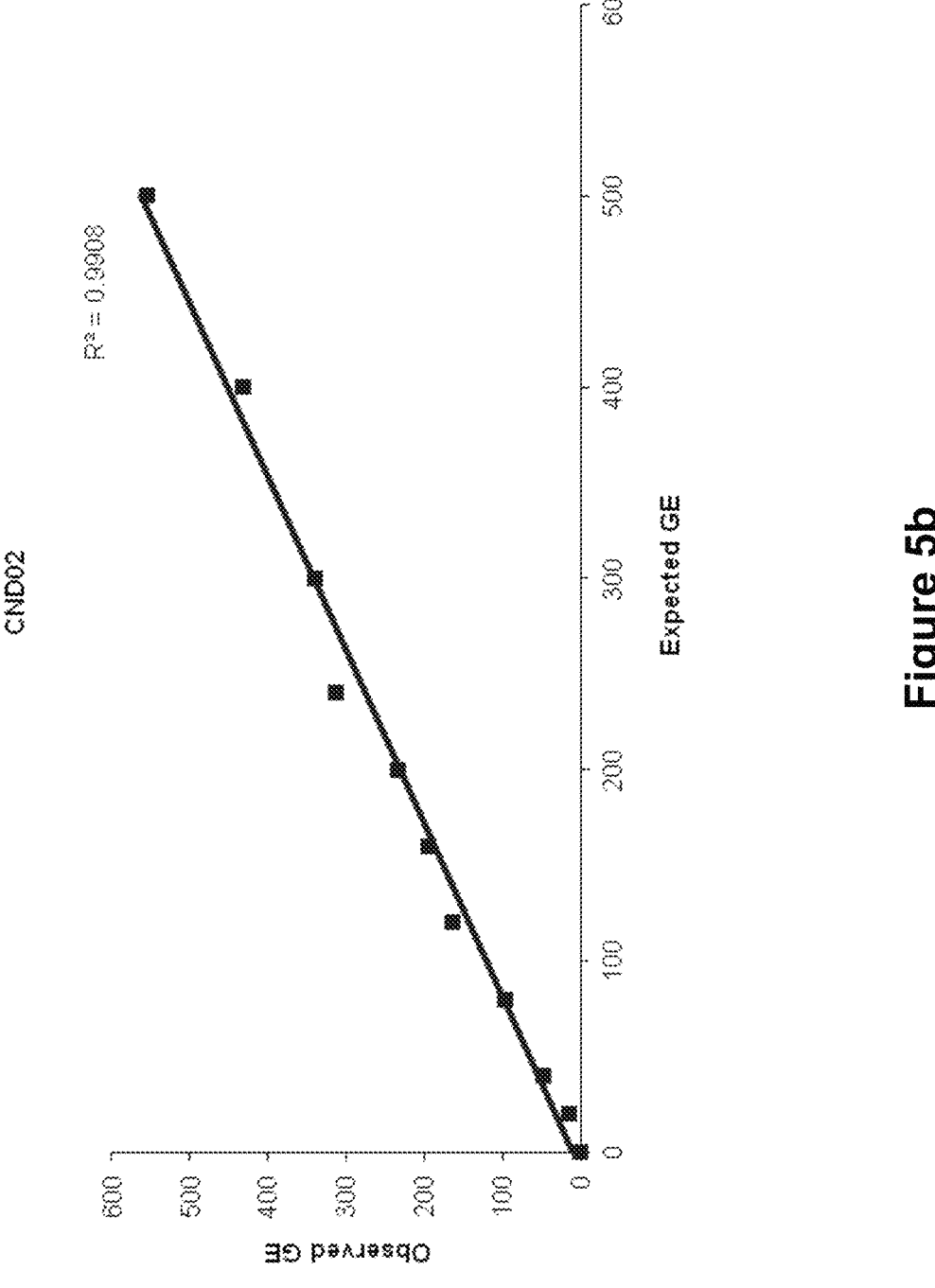
Figure 5C:
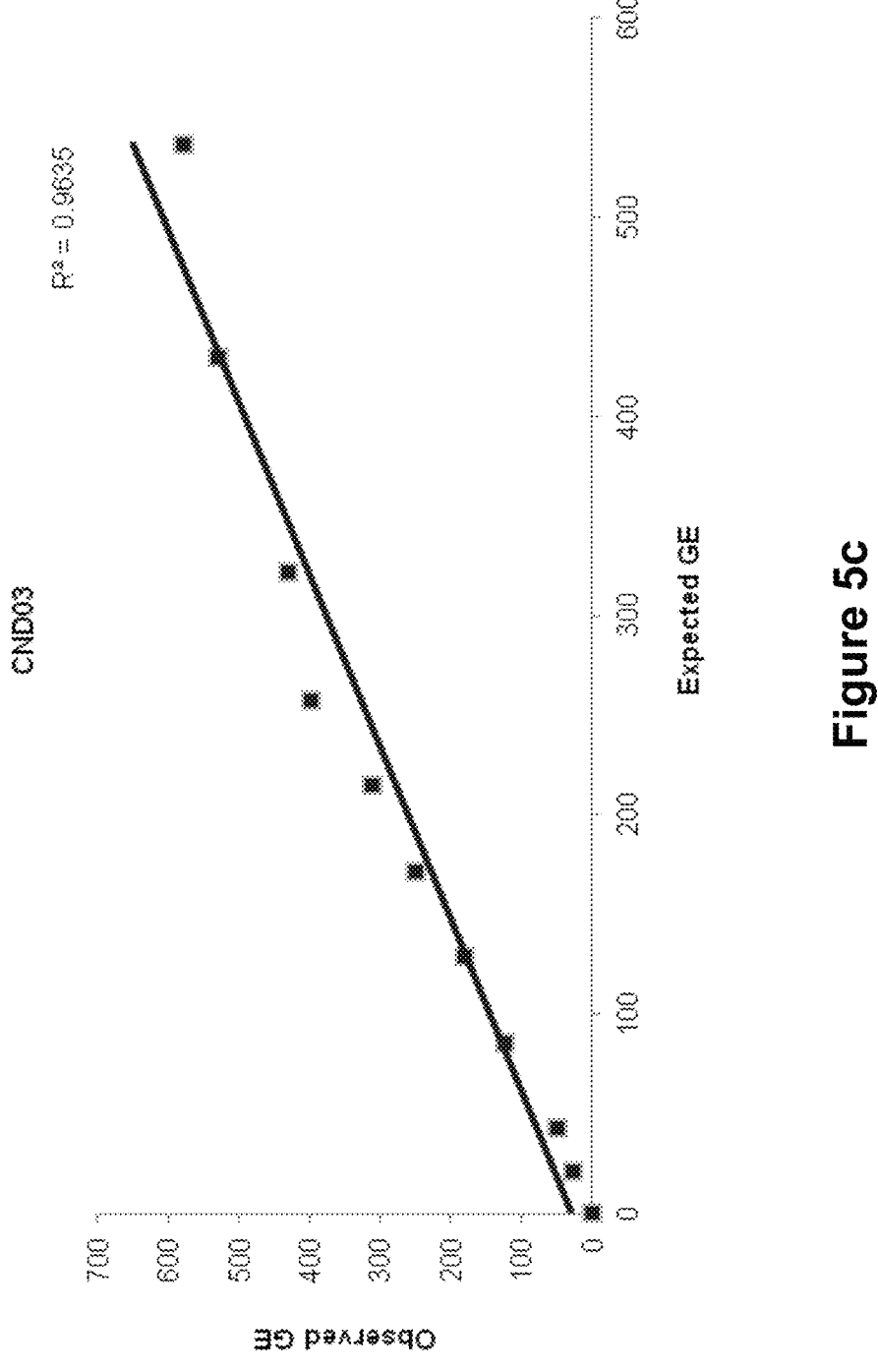

The sensitivity of the qPCR assays for measurement of a rare DNA species in a mixture of DNA was determined using 'spiking' experiments. For each qPCR assay in the panel, a control sample which is heterozygous (i.e. 1 copy) for the respective CND locus is 'spiked' into a nullisomic sample at a range (20-500) of haploid copies (i.e. genomic equivalents per reaction). The results in FIGS. 5*a, b, c* for CND01, CND02 and CND03 respectively show that the qPCR assays generate accurate, precise and robust measurements of the level of rare DNA in the mixture down to 20 GE per reaction.

Example 9

Figure 6:
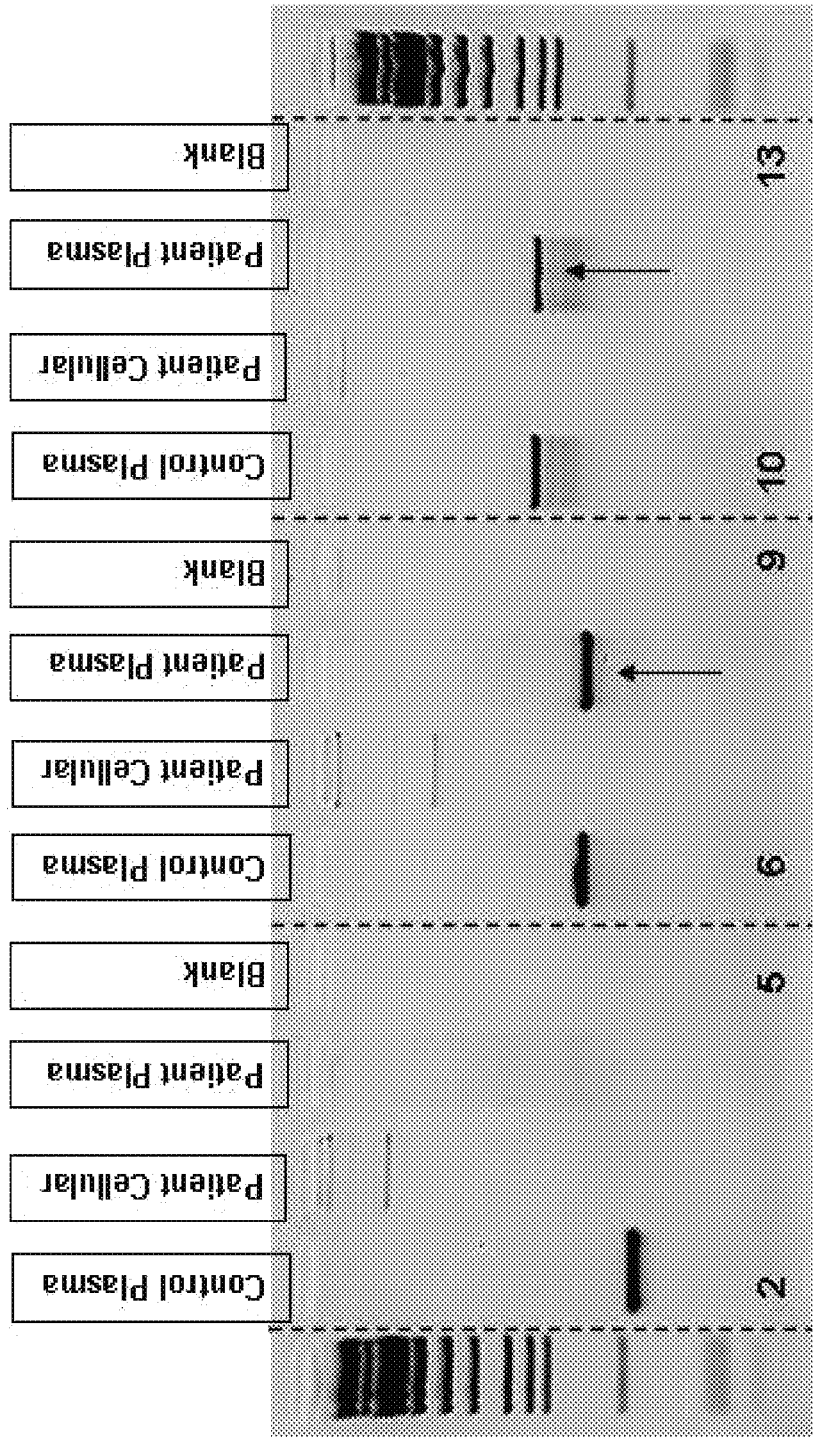
FIG. 6 is a photographic representation of internal PCR on cellular and plasma DNA for patient sample. Lanes 2-5 CND_02 (uninformative as both recipient and donor are 'null') lane 7-10 CND_03 (informative), lane 12-15 CND_08 (informative).

Detection of Donor (Non-Self) DNA in Plasma Samples from a Kidney Transplant Recipient A blood sample is collected from a patient manifesting clinical rejection. DNA is prepared from the leukocyte and plasma fractions and PCR assays specific for each of the panel 10 CNV-deletions run. The leukocyte DNA (self) is 'null' for CND_02, CND_03 and CND_08 (FIG. 6). Non-self PCR products (transplant-derived) are found in the plasma DNA for CND_03 and CND_08. No plasma product is found for CND_02 as the organ donor was presumably also 'null' for this CNV-deletion (the probability of the occurring is 1 in 2 [50%])).

The CND_03 and CND_08 PCR products from plasma were sequenced and shown by BLAT to match exactly with the expected respective genome sequences showing them to be unique and non-self in origin.

Example 10

Clinical Studies

Figure 7A:
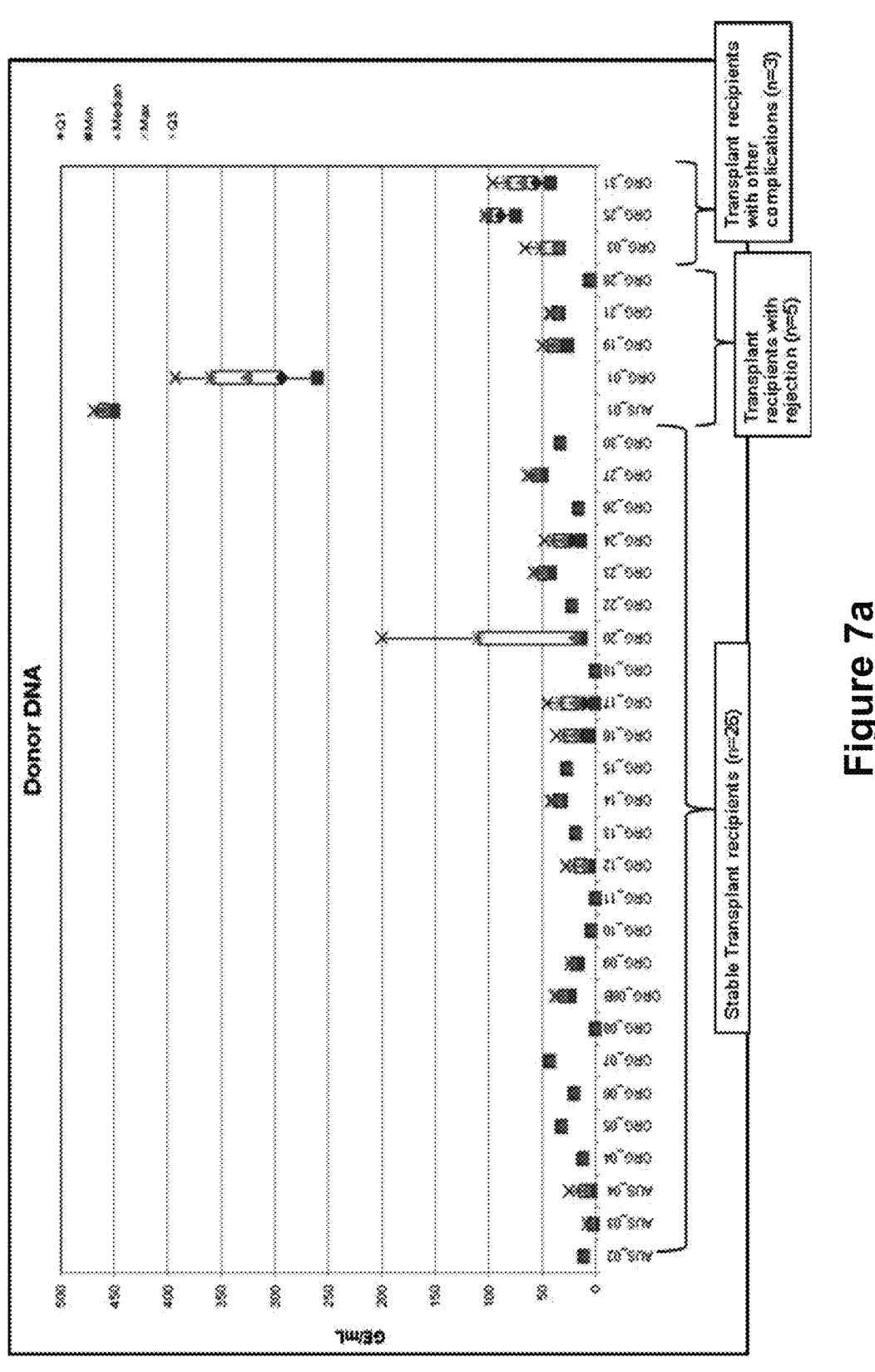
FIGS. 7a and 7b are graphical representations of plasma transplant-derived cDNA (a) and total cfDNA (b) for 35 transplant recipients. In the transplant recipients experiencing variable clinical signs of rejection, the donor-specific plasma DNA concentrations were found to vary and this appeared to correlate with the immunologic mechanism of rejection (i.e. humoral versus cellular mediated) as well as the medical category of rejection (i.e. acute versus chronic).
Figure 7B:
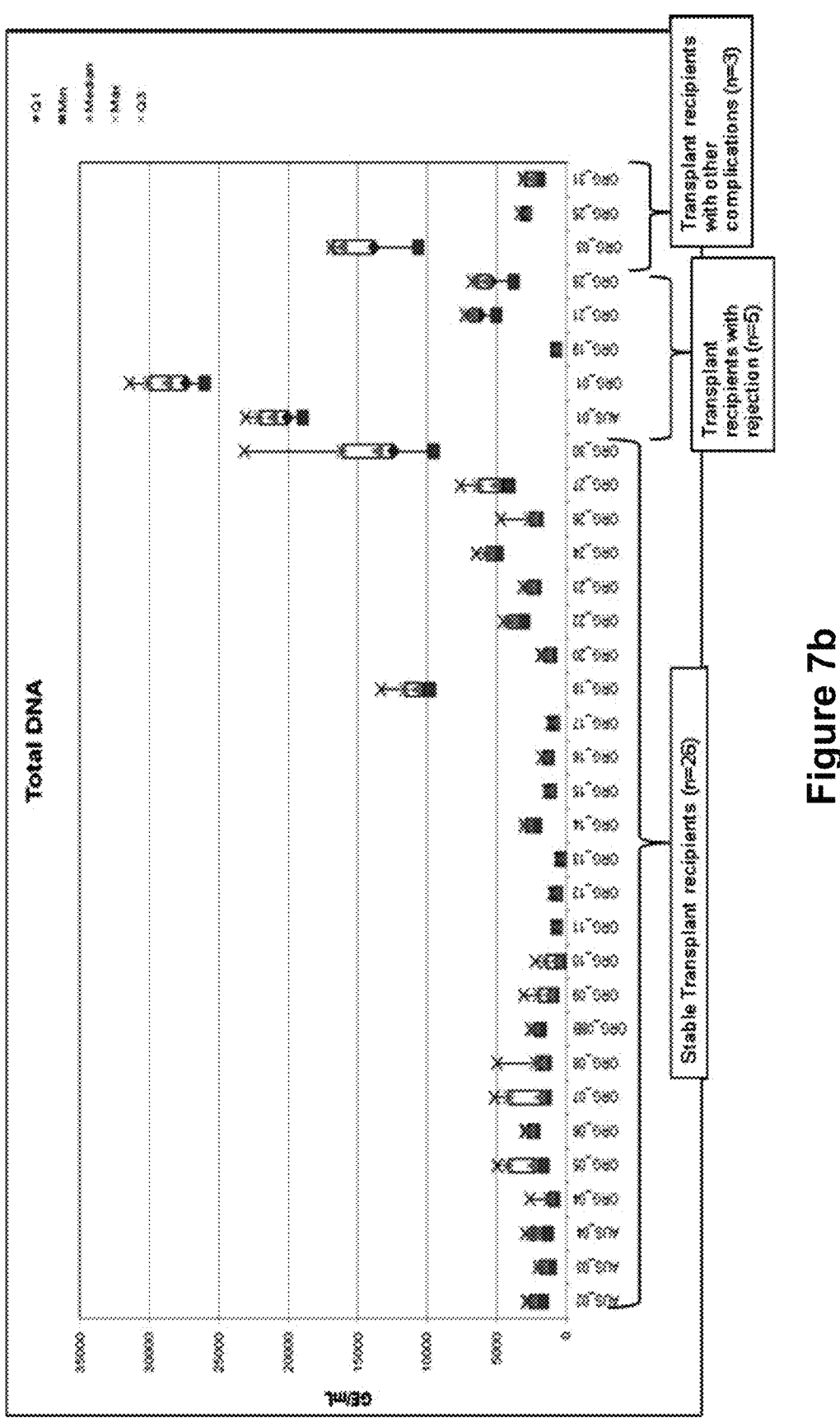

All recipients are first genotyped to determine genotype status for all CNV in the panel. CNV markers where the recipient is heterozygous for wild-type sequence are used to assay total plasma concentrations of self-DNA (a separate HBB qPCR assay is also used for this purpose). CNV markers where the recipient is 'null' and the donor is not are used to determine donor-specific plasma DNA concentrations in recipient plasma. The total recipient plasma DNA and the donor-specific plasma DNA were measured in 35 transplant recipients, including 26 stable transplant recipients, 6 transplant recipients experiencing variable clinical signs of rejection of which two showed very high-levels of circulating donor DNA (AUS_01 and ORG_01) and 3 transplant recipients experiencing other complications (ORG_03, ORG_25 and ORG_31). Measurements of plasma transplant-derived cfDNA and total plasma cfDNA for all 35 samples are shown in FIGS. 7*a* and 7*b*. In the six transplant recipients experiencing variable clinical signs of rejection, the donor-specific plasma DNA concentrations were found to vary and this appeared to correlate with the immunologic mechanism of rejection (i.e. humoral versus cellular mediated) as well as the medical category of rejection (i.e. acute versus chronic).

Example 11

Longitudinal Investigations in a Single Sample

Figure 8A:
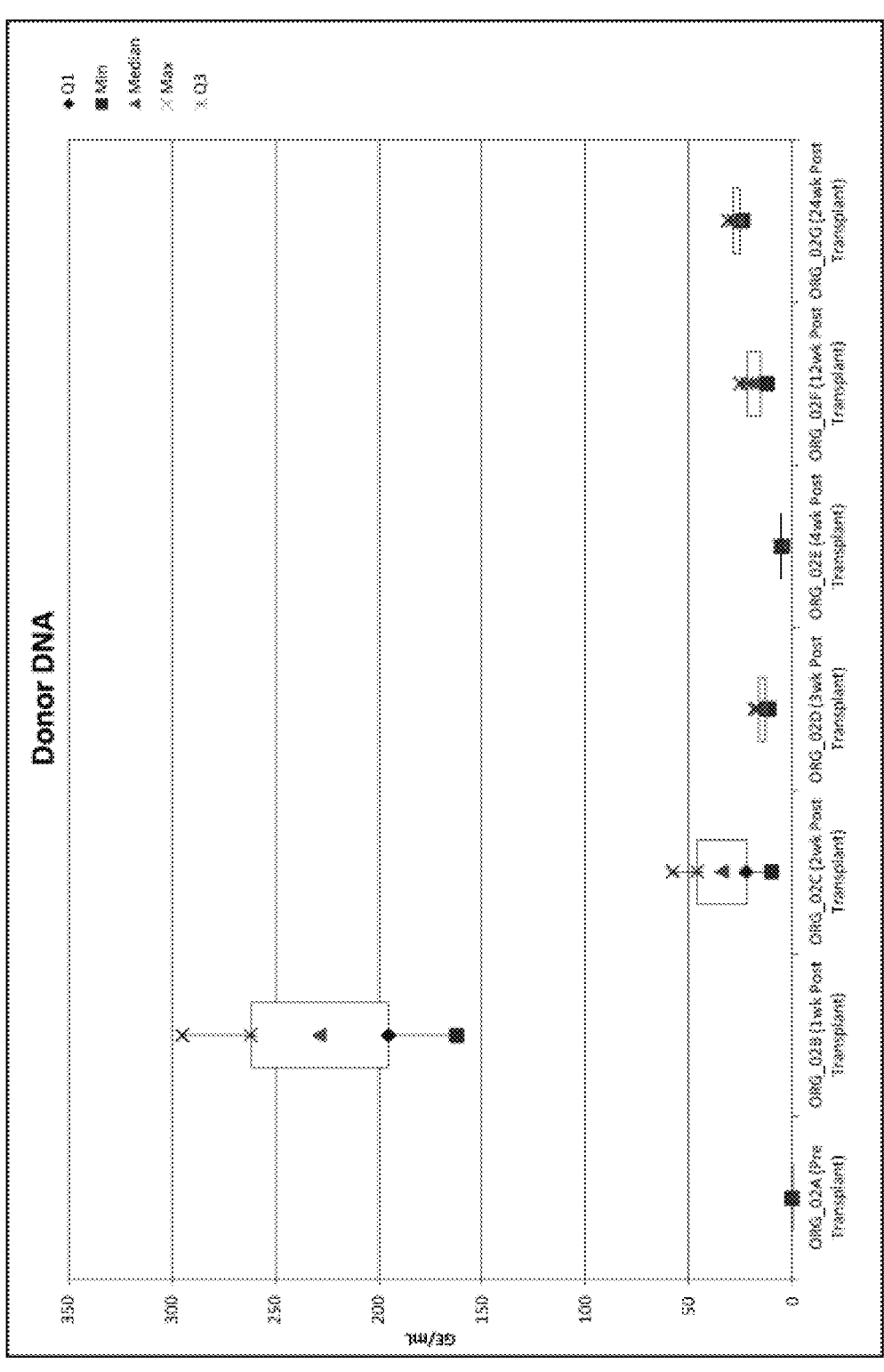
FIGS. 8a and 8b are graphical representations of plasma-derived cfDNA (a) and total plasma cfDNA (b) in pre-transplant and post-transplant recipients.
Figure 8B:
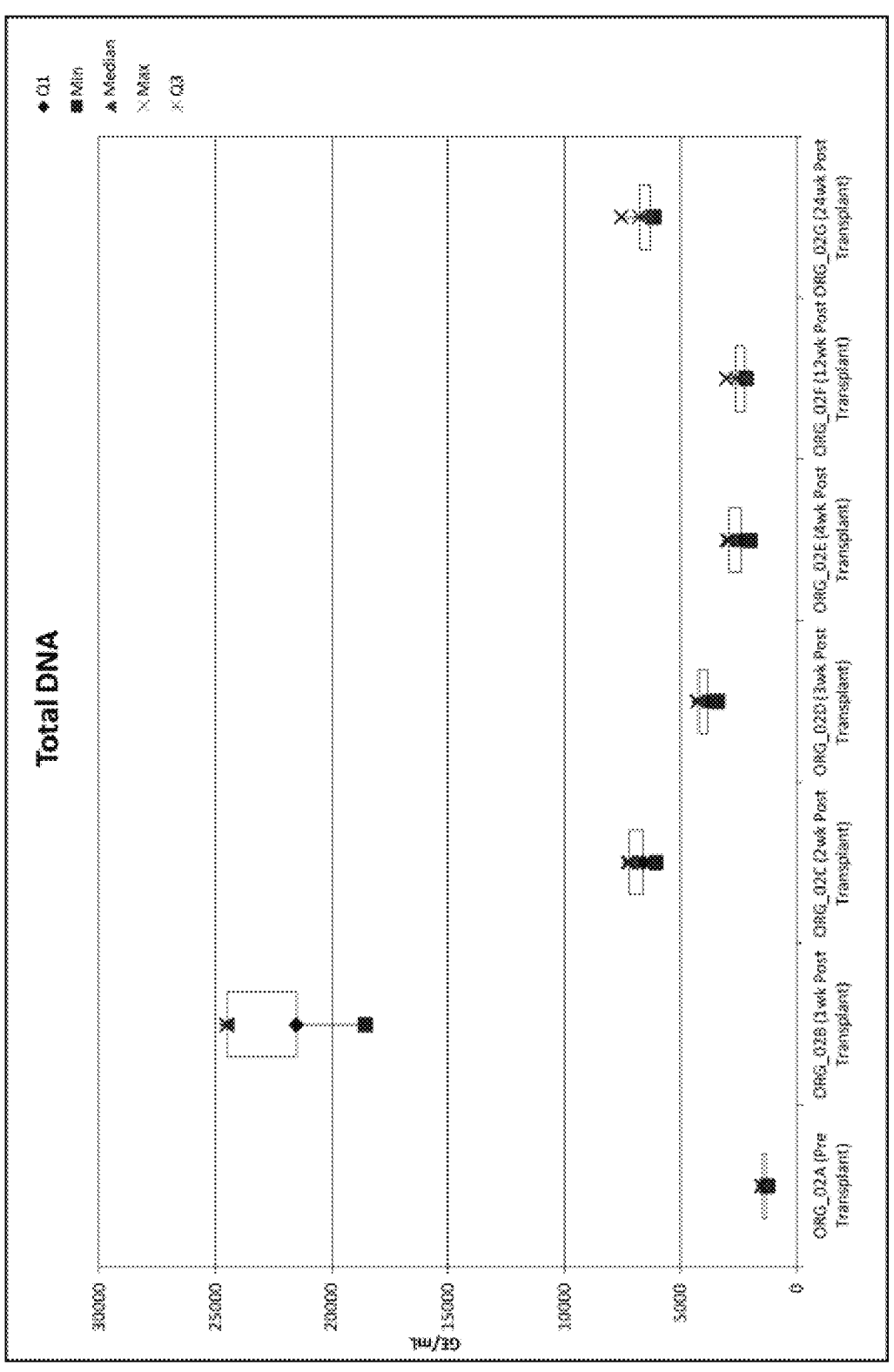

Informative qPCR assays were run on samples taken from a transplant recipient at the following time-points: pre-transplant, weekly for 4 weeks post-transplantation, at 12 weeks and at 24 weeks. Measurements of plasma transplant-derived cfDNA and total plasma cfDNA are shown in FIGS. 8a and 8b.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

Cass et al. (2010) *Kidney Health Australia* 27
Conrad et al. (2010) *Nature* 464:704-712
DeLa Vega et al. (2005) *Mutation Research* 573:111-135
Diehl et al. (2005) *Proc. Natl. Acad. Sci USA* 102:16368-16373
Diehl et al. (2008) *Nat. Med.* 14:985-990
Feuk et al. (2006) *Nature Rev* 7:85-97
Giacona et al. (1998) *Pancreas* 17:89-97
Gonzalez et al. (2005) *Environ. Michrobiol.* 7(7):1024-1028
Howard et al. (2009) *Nephrology* 14:123-132
Lee et al. (2006) *Transfusion* 46:1870-1878
Livak et al. (1995) *Nature Genetics* 9:341-342
Lo et al. (1998) *Am J Hum Genet* 62(4):768-75
McCarroll et al. (2008) *Nat Genet* 40(10):1166-1174
Mandel et al. (1948) *C.R. Acad. Sci Paris* 142:241-243
The 1000 Genomes Project Consortium (2010) *Nature* 467: 1061-1073
Weber et al. (2002) *Am J Human Genet* 71:854-862
Wu et al. (2009) *Nature Medicine* 15(2):215-219

What is claimed is:

1. A method, comprising:
   (a) extracting DNA comprising donor and recipient DNA fragments from a substantially cell-free sample of blood plasma, blood serum or urine of an organ transplant recipient;
   (b) amplifying the DNA extracted in (a) via an amplification reaction which selectively amplifies DNA comprising copy number deletion (CND) polymorphism(s) which indicate the DNA is donor-derived, wherein the amplified DNA after (b) comprises a detectable level of extracellular circulatory donor DNA fragments which comprise the CND polymorphism(s); and (c) quantifying the level of DNA comprising the CND polymorphism(s) which indicate the DNA is donor derived based on the results of the amplification reaction, wherein the CND(s) comprises at least one copy number variant polymorphism selected from the group consisting of CNP ID: CNVR358.1, CNVR217.1, CNVR483.1 CNVR451_full, CNVR376.1, CNVR381.1, 88, CNVR431.1, 262, CNVR1138.2, CNVR1138.3, CNVR966.1, CNVR1037.1, CNVR952.1, CNVR801_full, CNVR842.1, CNVR1041_full, CNVR1058.1, CNVR894.2, CNVR1648.2, CNVR1438_full, CNVR1576.1, CNVR1419.1, CNVR1685.1, CNVR1610.1, CNVR1341.1, CNVR1464.1, CNVR2196.1, CNVR1894.1, CNVR2221_full, CNVR1937.1, CNVR1935_full, CNVR1819.6, CNVR2172 full, CNVR2168 full, 726, CNVR2613_full, CNVR2535_full, CNVR2344_full, CNVR2469.1, CNVR2304.1, 896, CNVR2939.3, CNVR2939.2, CNVR2799.1, CNVR3004.1, CNVR2906.1, CNVR2972 full, CNVR2859 full, 933, CNVR3009.1, CNVR3472 full, CNVR3319.1, CNVR3495.1, 1103, CNVR3451.1, CNVR3609.1, CNVR3753_full, CNVR3935.1, CNVR4014.1, CNVR3831.1, CNVR3689.1, CNVR4250.1, CNVR4331.1, CNVR4374.1, CNVR4203.1, CNVR4332.1, CNVR4841.1, CNVR4665.1, CNVR4886.1, CNVR4596.1, CNVR4906.1, 1730, CNVR5122.1, CNVR5294.1, CNVR5429.1, CNVR5853 full, CNVR5923.1, CNVR5850.1, CNVR5871.1, CNVR6133.1, CNVR6211.1, CNVR6084.1, CNVR6074 full, CNVR6357.1, CNVR6540.1, CNVR6670.1, CNVR6676.1, CNVR6782.1, CNVR7144.1, CNVR7096.1, CNVR7301.1, CNVR7344.1, CNVR7543.1, CNVR7581 full, 2434, 2454, CNVR7808.1, CNVR7849.1, CNVR7796 full, 2559, CNVR8147.1, CNVR8114.4, and CNVR8154.1.

2. The method of claim 1, wherein the level of DNA comprising the CND polymorphism(s) which indicate the DNA is donor derived produced in (b) are not determined by nucleotide sequencing analysis or bi-allelic microchimerism analysis.

3. The method of claim 1, wherein the CND is CNVR376.1.

4. The method of claim 1, wherein the organ transplant recipient received an organ selected from the group consisting of a kidney, heart, lung, pancreatic islet, liver, intestine and skin.

5. The method of claim 1, wherein the organ transplant recipient received a kidney.

6. The method of claim 1, wherein the amplification reaction is digital PCR.

* * * * *